US010376258B2

(12) United States Patent
Cantor et al.

(10) Patent No.: US 10,376,258 B2
(45) Date of Patent: Aug. 13, 2019

(54) SURGICAL INTRODUCER WITH GUIDANCE SYSTEM RECEPTACLE

(71) Applicant: Vycor Medical, Inc., Boca Raton, FL (US)

(72) Inventors: David Cantor, Boca Raton, FL (US); Robert Schaefer, Riverside, CA (US)

(73) Assignee: Vycor Medical, Inc., Boca Raton, FL (US)

( * ) Notice: Subject to any disclaimer, the term of this patent is extended or adjusted under 35 U.S.C. 154(b) by 207 days.

(21) Appl. No.: 15/372,890

(22) Filed: Dec. 8, 2016

(65) Prior Publication Data

US 2018/0125471 A1 May 10, 2018

Related U.S. Application Data

(60) Provisional application No. 62/418,507, filed on Nov. 7, 2016.

(51) Int. Cl.
*A61B 17/02* (2006.01)
*A61B 90/00* (2016.01)
(Continued)

(52) U.S. Cl.
CPC ...... *A61B 17/0218* (2013.01); *A61B 17/3421* (2013.01); *A61B 90/361* (2016.02); (Continued)

(58) Field of Classification Search
CPC ....... A61B 1/32; A61B 17/02; A61B 17/0218; A61B 17/34; A61B 17/3415; (Continued)

(56) References Cited

U.S. PATENT DOCUMENTS

| 1,849,701 A | 3/1932 | Allyn |
| 2,769,441 A | 11/1956 | Abramson |

(Continued)

FOREIGN PATENT DOCUMENTS

| CN | 203724147 | 7/2014 |
| DE | 102005032197 | 1/2007 |

(Continued)

OTHER PUBLICATIONS

Extended European Search Report for EP 08 840 022.5, The Hague, dated Mar. 18, 2013, 7 pages.
(Continued)

*Primary Examiner* — Andrew Yang
(74) *Attorney, Agent, or Firm* — RatnerPrestia

(57) ABSTRACT

A surgical introducer system having a sidewall that forms an introducer passage, and a probe receptacle located at the distal end of the introducer. The probe receptacle has an inner surface having a first lateral size at a proximal receptacle end and a second lateral size in the lateral direction at the distal receptacle end, and the first lateral size is greater than the second lateral size. The inner surface receives the distal tip of a navigation probe and restricts movement of the distal probe tip in the lateral direction, and the sidewall is spaced from the navigation probe shaft to allow the shaft to move in the lateral direction within the passage when the distal probe tip is positioned in the probe receptacle.

35 Claims, 9 Drawing Sheets

(51) Int. Cl.
*A61B 17/34* (2006.01)
*A61B 17/00* (2006.01)
*A61B 34/20* (2016.01)

(52) U.S. Cl.
CPC ...... *A61B 90/39* (2016.02); *A61B 2017/0046* (2013.01); *A61B 2017/00907* (2013.01); *A61B 2034/2051* (2016.02); *A61B 2034/2068* (2016.02); *A61B 2090/3945* (2016.02); *A61B 2090/3954* (2016.02); *A61B 2090/3958* (2016.02); *A61B 2090/3983* (2016.02)

(58) Field of Classification Search
CPC ............ A61B 17/3417; A61B 17/3421; A61B 17/3423; A61B 34/20; A61B 2034/20
See application file for complete search history.

(56) References Cited

U.S. PATENT DOCUMENTS

| | | |
|---|---|---|
| 2,922,415 A | 1/1960 | Campagna |
| 3,417,746 A | 12/1968 | Moore |
| 3,608,547 A | 9/1971 | Sato |
| 3,626,471 A | 12/1971 | Florin |
| 3,690,323 A | 9/1972 | Wortman |
| 3,766,910 A | 10/1973 | Lake |
| 3,789,829 A | 2/1974 | Hasson |
| 3,882,855 A | 5/1975 | Schulte |
| 3,888,117 A | 6/1975 | Lewis |
| 4,263,900 A | 4/1981 | Nicholson |
| 4,312,353 A | 1/1982 | Shahbabian |
| 4,386,602 A | 6/1983 | Sheldon |
| 4,502,468 A | 3/1985 | Burgin |
| 4,585,438 A | 4/1986 | Makler |
| 4,636,199 A | 1/1987 | Victor |
| 4,638,798 A | 1/1987 | Shelden |
| 4,742,815 A | 5/1988 | Ninan et al. |
| 4,931,039 A | 6/1990 | Coe |
| 4,945,896 A | 8/1990 | Gade |
| 5,052,373 A | 10/1991 | Michelson |
| 5,135,526 A | 8/1992 | Zinnanti |
| 5,160,323 A | 11/1992 | Andrew |
| 5,183,464 A | 2/1993 | Dubrul |
| 5,230,623 A | 7/1993 | Guthrie |
| 5,249,568 A | 10/1993 | Brefka |
| 5,251,127 A | 10/1993 | Raab |
| 5,256,149 A | 10/1993 | Banik |
| 5,271,380 A | 12/1993 | Riek |
| 5,275,583 A | 1/1994 | Crainich |
| 5,284,130 A | 2/1994 | Ratliff |
| 5,305,203 A | 4/1994 | Raab |
| 5,320,611 A | 6/1994 | Bonutti |
| 5,334,150 A | 8/1994 | Kaali |
| 5,356,421 A | 10/1994 | Castro |
| 5,376,076 A | 12/1994 | Kaali |
| 5,380,291 A | 1/1995 | Kaali |
| 5,431,151 A | 7/1995 | Riek |
| 5,431,676 A | 7/1995 | Dubrul |
| 5,441,041 A | 8/1995 | Sauer |
| 5,445,142 A | 8/1995 | Hassler, Jr. |
| 5,467,762 A | 11/1995 | Sauer |
| 5,513,238 A | 4/1996 | Leber |
| 5,540,711 A | 7/1996 | Kieturakis |
| 5,551,947 A | 9/1996 | Kaali |
| 5,555,283 A | 9/1996 | Shiu |
| 5,562,696 A | 10/1996 | Nobles |
| 5,569,160 A | 10/1996 | Sauer |
| D377,093 S | 12/1996 | Michelson |
| 5,591,192 A | 1/1997 | Privitera |
| 5,609,562 A | 3/1997 | Kaali |
| 5,658,236 A | 8/1997 | Sauer |
| 5,662,111 A | 9/1997 | Cosman |
| 5,665,072 A | 9/1997 | Yoon |
| 5,676,673 A | 10/1997 | Ferre |
| 5,685,820 A | 11/1997 | Riek |
| 5,702,761 A | 12/1997 | DiChiara, Jr. |
| 5,738,628 A | 4/1998 | Sierocuk |
| 5,748,703 A | 5/1998 | Cosman |
| 5,748,767 A | 5/1998 | Raab |
| 5,762,629 A | 6/1998 | Kambin |
| 5,778,043 A | 7/1998 | Cosman |
| 5,782,807 A | 7/1998 | Falvai |
| 5,785,648 A | 7/1998 | Min |
| 5,792,044 A | 8/1998 | Foley |
| 5,800,352 A | 9/1998 | Ferre |
| 5,803,089 A | 9/1998 | Ferre |
| 5,829,444 A | 11/1998 | Ferre |
| 5,846,249 A | 12/1998 | Thompson |
| 5,848,967 A | 12/1998 | Cosman |
| 5,860,996 A | 1/1999 | Urban |
| 5,873,822 A | 2/1999 | Ferre |
| 5,891,157 A | 4/1999 | Day et al. |
| 5,902,272 A | 5/1999 | Eggers |
| 5,921,992 A | 7/1999 | Costales |
| 5,947,981 A | 9/1999 | Cosman |
| 5,967,970 A | 10/1999 | Cowan |
| 5,967,980 A | 10/1999 | Ferre |
| 5,971,997 A | 10/1999 | Guthrie |
| 6,005,919 A | 12/1999 | Kooy |
| 6,006,126 A | 12/1999 | Cosman |
| 6,007,481 A | 12/1999 | Riek |
| 6,041,101 A | 3/2000 | Kooy |
| 6,047,218 A | 4/2000 | Whayne |
| 6,083,191 A | 7/2000 | Rose |
| 6,093,145 A | 7/2000 | VomBerg |
| 6,096,038 A | 8/2000 | Michelson |
| 6,120,465 A | 9/2000 | Guthrie |
| 6,129,685 A | 10/2000 | Howard, III |
| 6,142,931 A | 11/2000 | Kaji |
| 6,156,054 A | 12/2000 | Zadno-Azizi |
| 6,159,178 A | 12/2000 | Sharkawy |
| 6,167,295 A | 12/2000 | Cosman |
| 6,175,756 B1 | 1/2001 | Ferre |
| 6,179,826 B1 | 1/2001 | Aebischer |
| 6,214,017 B1 | 4/2001 | Stoddard |
| 6,221,078 B1 | 4/2001 | Bylsma |
| 6,224,599 B1 | 5/2001 | Baynham |
| 6,228,059 B1 | 5/2001 | Astarita |
| 6,236,875 B1 | 5/2001 | Bucholz |
| 6,245,052 B1 | 6/2001 | Orth |
| 6,256,859 B1 | 7/2001 | Stoddard |
| 6,259,943 B1 | 7/2001 | Cosman |
| 6,275,725 B1 | 8/2001 | Cosman |
| 6,277,069 B1 | 8/2001 | Gray |
| 6,278,766 B1 | 8/2001 | Kooy |
| 6,283,912 B1 | 9/2001 | Hu |
| 6,293,952 B1 | 9/2001 | Brosens |
| 6,296,647 B1 | 10/2001 | Robioneck |
| 6,326,875 B1 | 12/2001 | Tuovinen |
| 6,331,180 B1 | 12/2001 | Cosman |
| 6,341,231 B1 | 1/2002 | Ferre |
| 6,351,661 B1 | 2/2002 | Cosman |
| 6,359,959 B1 | 3/2002 | Butler |
| 6,364,832 B1 | 4/2002 | Propp |
| 6,371,964 B1 | 4/2002 | Vargas |
| 6,374,135 B1 | 4/2002 | Bucholz |
| 6,383,191 B1 | 5/2002 | Zdeblick |
| 6,405,072 B1 | 6/2002 | Cosman |
| 6,409,686 B1 | 6/2002 | Guthrie |
| 6,416,520 B1 | 7/2002 | Kynast |
| 6,425,859 B1 | 7/2002 | Foley |
| 6,445,944 B1 | 9/2002 | Ostrovsky |
| 6,459,769 B1 | 10/2002 | Cosman |
| 6,461,330 B1 | 10/2002 | Miyagi |
| 6,478,028 B1 | 11/2002 | Paolitto |
| 6,478,806 B2 | 11/2002 | McFarlane |
| 6,551,240 B2 | 4/2003 | Henzler |
| 6,565,574 B2 | 5/2003 | Michelson |
| 6,589,211 B1 | 7/2003 | MacLeod |
| 6,595,917 B2 | 7/2003 | Nieto |
| 6,596,008 B1 | 7/2003 | Kambin |
| 6,599,292 B1 | 7/2003 | Ray |
| 6,602,227 B1 | 8/2003 | Cimino |
| 6,605,036 B1 | 8/2003 | Wild |

(56) References Cited

U.S. PATENT DOCUMENTS

| | | |
|---|---|---|
| 6,654,999 B2 | 12/2003 | Stoddard |
| 6,662,036 B2 | 12/2003 | Cosman |
| 6,669,685 B1 | 12/2003 | Rizoiu |
| 6,675,040 B1 | 1/2004 | Cosman |
| 6,685,630 B2 | 2/2004 | Sauer |
| 6,761,687 B1 | 7/2004 | Doshi |
| D495,053 S | 8/2004 | Laun |
| 6,863,674 B2 | 3/2005 | Kasahara |
| 6,896,680 B2 | 5/2005 | Michelson |
| 6,942,634 B2 | 9/2005 | Odland |
| 7,081,089 B2 | 7/2006 | Bonadio |
| 7,153,304 B2 | 12/2006 | Robie |
| 7,235,084 B2 | 6/2007 | Skakoon |
| 7,449,011 B2 | 11/2008 | Wenchell et al. |
| 7,474,820 B2 | 1/2009 | Vayser |
| 7,479,150 B2 | 1/2009 | Rethy et al. |
| 7,510,524 B2 | 3/2009 | Vayser |
| 7,686,492 B2 | 3/2010 | Vayser |
| 8,360,970 B2 | 1/2013 | Mangiardi |
| 8,386,052 B2 | 2/2013 | Harris |
| 8,409,083 B2 | 4/2013 | Mangiardi |
| 8,608,650 B2 | 12/2013 | Mangiardi |
| 8,608,769 B2 | 12/2013 | Kahle |
| 8,679,088 B2 | 3/2014 | Abrahams |
| 9,216,015 B2 | 12/2015 | Wilson |
| 9,307,969 B2 | 4/2016 | Novak |
| 2001/0010002 A1 | 7/2001 | Michelson |
| 2001/0027271 A1 | 10/2001 | Franck |
| 2001/0037050 A1 | 11/2001 | Lemperle |
| 2002/0022764 A1 | 2/2002 | Smith |
| 2002/0151769 A1 | 10/2002 | Kim |
| 2002/0161366 A1 | 10/2002 | Robie |
| 2003/0040753 A1 | 2/2003 | Daum |
| 2003/0073934 A1 | 4/2003 | Putz |
| 2003/0139648 A1 | 7/2003 | Foley |
| 2003/0145865 A1 | 8/2003 | Sterman |
| 2004/0024291 A1 | 2/2004 | Zinkel |
| 2004/0059375 A1 | 3/2004 | Ginn |
| 2004/0068172 A1 | 4/2004 | Nowinski |
| 2004/0097792 A1 | 5/2004 | Moll |
| 2004/0102804 A1 | 5/2004 | Chin |
| 2004/0186346 A1 | 9/2004 | Smith |
| 2004/0230100 A1 | 11/2004 | Shluzas |
| 2005/0273132 A1 | 12/2005 | Shluzas |
| 2005/0277811 A1 | 12/2005 | Richards |
| 2006/0041270 A1 | 2/2006 | Lenker |
| 2006/0122462 A1 | 6/2006 | Roth |
| 2006/0212062 A1 | 9/2006 | Farascioni |
| 2006/0287583 A1 | 12/2006 | Mangiardi |
| 2007/0129747 A1 | 6/2007 | Dorman |
| 2007/0135679 A1 | 6/2007 | Hunt |
| 2007/0232874 A1 | 10/2007 | Ince |
| 2008/0100061 A1 | 5/2008 | Sage |
| 2008/0109026 A1 | 5/2008 | Kassam |
| 2008/0119693 A1 | 5/2008 | Makower |
| 2009/0048622 A1 | 2/2009 | Wilson |
| 2009/0312611 A1 | 12/2009 | Mangiardi |
| 2010/0010315 A1 | 1/2010 | Mangiardi |
| 2011/0118710 A1 | 5/2011 | Begemann et al. |
| 2011/0160672 A1 | 6/2011 | Boebel et al. |
| 2011/0196205 A1 | 8/2011 | Hathaway et al. |
| 2011/0301424 A1 | 12/2011 | Steigerwald |
| 2012/0016204 A1 | 1/2012 | Bastia |
| 2012/0016316 A1 | 1/2012 | Zhuang |
| 2012/0035424 A1 | 2/2012 | Schulte |
| 2012/0071748 A1* | 3/2012 | Mark .............. A61B 17/3421 600/411 |
| 2012/0253375 A1 | 10/2012 | Mark |
| 2012/0266058 A1 | 10/2012 | Carrascosa |
| 2012/0289816 A1 | 11/2012 | Mark |
| 2013/0066154 A1 | 3/2013 | Mangiardi |
| 2013/0102851 A1 | 4/2013 | Mark |
| 2013/0102886 A1 | 4/2013 | Mark |
| 2013/0204095 A1 | 8/2013 | Mark |
| 2013/0204287 A1 | 8/2013 | Mark |
| 2013/0211200 A1 | 8/2013 | Brannon |
| 2013/0245381 A1 | 9/2013 | Deng et al. |
| 2014/0107426 A1 | 4/2014 | Wilson |
| 2014/0171873 A1 | 6/2014 | Mark |
| 2014/0187922 A1 | 7/2014 | Mark |
| 2016/0015374 A1* | 1/2016 | Gifford .............. A61B 17/3415 600/201 |
| 2016/0317182 A1 | 11/2016 | Mark |
| 2017/0000579 A1 | 1/2017 | Mark |
| 2017/0265893 A1 | 9/2017 | Mark et al. |
| 2017/0265894 A1 | 9/2017 | Mark et al. |
| 2017/0360291 A1 | 12/2017 | Chegini et al. |
| 2018/0014890 A1 | 1/2018 | Stanton et al. |
| 2018/0085182 A1 | 3/2018 | Ewers et al. |
| 2018/0125603 A1 | 5/2018 | Cantor et al. |
| 2018/0161024 A1 | 6/2018 | Davis et al. |

FOREIGN PATENT DOCUMENTS

| | | |
|---|---|---|
| JP | 02289221 | 11/1990 |
| JP | 05344978 | 12/1993 |
| JP | 9224943 | 9/1997 |
| JP | 2000287915 | 10/2000 |
| JP | 2003153907 | 5/2003 |
| RU | 349136 | 9/1972 |
| RU | 45928 | 6/2005 |
| RU | 55570 | 8/2006 |
| SU | 131027 | 3/1959 |
| SU | 585840 | 1/1978 |
| SU | 1521465 | 11/1989 |
| WO | 2001043627 | 6/2001 |
| WO | 2006050225 | 1/2006 |
| WO | 2006017507 | 2/2006 |
| WO | 2006050047 | 5/2006 |
| WO | 2013063027 | 1/2013 |
| WO | 2014137530 | 1/2014 |
| WO | 2014137551 | 1/2014 |

OTHER PUBLICATIONS

Greenfield, et al. "Stereotactic Minimally Invasive Tubular Retractor System for Deep Brain Lesions," Operative Neurosurgery 2, vol. 63, Oct. 2008, pp. 334-340. 7 pages.

Decision for Rejection for Patent Application No. 2009-539227 dated May 31, 2013, 8 pages.

Alberti, O., et al., "Frameless navigation and endoscopy," Journal of Neurosurgery, Sep. 2001; 95(3): 541-3. Abstract only.

Amstutz, C., et al., "A-Mode Ultrasound-Based Registration in Computer-Aided Surgery of the Skull," Arch Otolaryngol Head Neck Surg. 2003; 129(12):1310-1316.

Andrews, R.J., et al., "A review of brain retraction and recommendations for minimizing intraoperative brain injury," Neurosurgery 1993; 33(6): 1052-1063.

Burtscher, J., et al., "Neuroendoscopy Based on Computer Assisted Adjustment of the Endoscope Holder in the Laboratory.," Minimum Invasive Neurosurgery 2003; 46:208-214.

Eldeib, A.M., et al., "Rigid neuroendoscope navigation system for minimally invasive surgery," Engineering in Medicine and Biology, 1999. Abstract only.

Fukamachi, A., et al., "Postoperative intracerebral hemorrhages: a survey of computed tomographic findings after 1074 intracranial operations," Surgery Neurol 1985; 23(6); 575-580. Abstract only.

Greenfield, JP, et al., "Stereotactic minimally invasive tubular retractor system for deep brain lesions," Neurosurgery 2008; 63(4): 334-339. Abstract only.

Gumprecht, H., et al., "Neuroendoscopy Combined with Frameless Neuronavigation," 2000, pp. 129-131, 14(2), British Journal of Neurosurgery.

Hilton et al., "METRx Microdiscectomy Surgical Technique," Medtronic Sofamor Danek publication, 2001, 20 pages.

Hellwig, D., et al. "Neuroendoscopic Treatment for Colloid Cysts of the Third Ventricle: The Experience of a Decade," Neurosurgery, Mar. 2003; 52(3):525-533. Abstract only.

Konen, W., et al., "An Image-Based Navigation Support System for Neuroendoscopic surgery," R. Ahlers (ed.) 5. Symposium Bilderarbeitung 1997, Technische Akademie Essingen. pp. 1-8.

(56) References Cited

OTHER PUBLICATIONS

Kubo, S., et al., "A Newly Designed Disposable Introducer Sheath for a Ventricular Fiberscope," Minimum Invasive Neurosurgery 2004; 47(2): 124-126. Abstract only.
Lemole, G.M., et al., "Cranial Application of Frameless Stereotaxy," Barrow Neuological Institute 2001; 17(1): 1-12.
McInerney, J., et al., "Frameless Stereotaxy of the Brain," The Mount Sinai Journal of Medicine 2000; 67(1): 300-310.
Mettler, L., et al., "Optical trocar systems: laparpscopic entry and its complications (a study of cases in Germany)," Gynaecological Endoscopy 1999; 8(6): 383-389. Abstract only.
Ogura, K., et al., "New microsurgical technique for intraparenchymal lesions of the brain: transcylincer approach," Aeta Neurochirurgica (Wien) 2006; 148: 779-785.
Otsuku, T., et al., "Stereotactic Guiding Tube for Open-System Endoscopy: A New Approach for Stereotactic Endoscopic Resection of Intra-Axial Brain Tumors," Neurosurgery 1990; 27(2): 326-330.
Rampini, P., et al., "Stereotactically guided endoscopy for the treatment of arachnoid cysts." Pediatric Neurosurgery 1998; 29(2): 102-104. Abstract only.
Kelly, et al. "The stereotaxic retractor in computer-assisted stereotaxic microsurgery," Journal of Neurosurgery, vol. 69, Aug. 1988, pp. 301-307, 7 pages.
Ross, D.A., "A simple stereotactic retractor for use with the Leksell stereotactic system," Neurosurgery 1993; 32(3): 475-476. Abstract only.
Scholz, M., et al., "Development of an Endoscopic Navigation System Based on Digital Image Processing," Computer Aided Surgery 1998; 3(3): 134-143. Abstract only.
Scholz, M., et al., "Virtual image navigation: a new method of control intraoperative bleeding in neuroendoscopic surgery," Neurosurg Focus 2000; 8(6): 1-8.
Spetzger, U., et al., "Navigational microneurosurgery: experience with Easy Guide Neuro," Medicamundi 1997; 41(1): 28-35.
UPMC: Minimally Invasive Brain Surgery. Legacy of Innovations. Breakthroughs in minimally invasive brain surgery at UPMC. 2014, 1 page.
Zhong, J., et al., "Brain retraction injury," Neurological Research 2003; 25: 831-838.
Entire patent prosecution history of U.S. Appl. No. 11/155,175, filed Jun. 17, 2005, entitled, "Surgical Access Instruments for Use With Delicate Tissues.".
Entire patent prosecution history of U.S. Appl. No. 12/545,686, filed Aug. 29, 2009, entitled, "Surgical Access Instruments for Use With Delicate Tissues."
Entire patent prosecution history of U.S. Appl. No. 13/431,280, filed Mar. 27, 2012, entitled, "Tissue Retractor Apparatus and Methods."
Alexander, et al. "Chapter 20: Stereotactic Frame Systems: The COMPASS System," Advanced Neurosurgical Navigation, 1999, pp. 267-277. 13 pages.
International Preliminary Report on Patentability and Written Opinion for International Application No. PCT/US2006/061246 dated Jun. 3, 2009, 5 pages.
"Neuronavigation" from Wikipedia dated Jul. 30, 2014, 2 pages.
OShaughnessy, P., "New Brain tumor technology helps man who took two bullets to the head return to normal life," Daily News, Jun. 19, 2011, 2 pages.
Preliminary Amendment and Request for Interference for U.S. Appl. No. 14/134,360 dated Dec. 23, 2013, 8 pages.
K060973 510(k) Summary, Jul. 26, 2006, 6 pages.
K043602 510(k) Summary, Feb. 23, 2005, 5 pages.
Entire patent prosecution history of U.S. Appl. No. 12/545,719, filed Aug. 21, 2009, entitled, "Surgical Access Methods for Use With Delicate Tissues," now U.S. Pat. No. 8,409,083, issued Apr. 2, 2013.
Engh, et al. NeuroendoportSM surgery facilitates removal of hard-to-reach brain tumors, University of Pittsburgh Neurosurgery News, vol. 10, No. 2, 2009. 8 pages.
Entire patent prosecution history of U.S. Appl. No. 13/674,507, filed Nov. 12, 2012, entitled, "Tissue Retractor Apparatus and Methods."
Entire patent prosecution history of U.S. Appl. No. 11/665,667, filed Apr. 18, 2007, entitled, "Apparatus and methods for performing brain surgery."
Entire patent prosecution history of U.S. Appl. No. 14/134,360, filed Dec. 9, 2013, entitled, "Apparatus and Methods for Performing Brain Surgery."
Slavin et al., "Testimonials," no date but admitted as prior art between Jun. 17, 2005 and Mar. 27, 2012, 4 pages.
Vycor Medical, "Vycor ViewSite TC: Endoscopic Intraparenchimal Brain Tumor Resection with Image Guidance," 2 pages, no date but admitted as prior art between Jun. 17, 2005 and Mar. 27, 2012.
Herrera, S. et al., "Use of Transparent Plastic Tubular Retractor in Surgery for Deep Brain Lesions: A Case Series," Surgical Technology International XIX, pp. 1-4, published in 2010.
Office Action dated Jul. 7, 2015 for U.S. Appl. No. 14/134,360, 23 pages.
Office Action dated Jul. 27, 2015 for U.S. Appl. No. 13/674,507, 11 pages.
International Search Report and Written Opinion for International Application No. PCT/US2015/030528 dated Aug. 14, 2015, 8 pages.
Raza.et al. "Minimally Invasive Trans-Portal Resection of Deep Intracranial Lesions," Minimally Invasive Neurosurgery, vol. 54, Feb. 2011, pp. 1-7.
Wang, W.H. et al., "Endoscopic hematoma evacuation in patients with spontaneous supratentorial intracerebral hemorrhage," Journal of the Chinese Medical Associations, vol. 78, 2015, pp. 101-107.
Tao, X. et al., "Microsurgical resection for lateral ventrical meningiomas with neuronavigation and tubular retractor system," Chin. J. Neurosurg, vol. 31, No. 4, 2015, pp. 332-336 (abstract only).
Rymarczuk, G.N. et al., "Use of a Minimally Invasive Retractor System for Retrieval of Intracranial Fragments in Wartime Trauma," World Neurosurgery, 2015, pp. 1-26.
Shoakazemi, A. et al., "A 3D endoscopic transtublar transcallosal approach to the third ventricle," J. Neurosurg, 2015, pp. 1-10.
Nagatani, K. et al., "High-Definition Exoscope System for Microneurosurgery: Use of an Exoscope in Combination with Tubular Retraction and Frameless Neuronavigation for Microsurgical Resection of Deep Brain Lesions," No Shinkei Geka, Jul. 2015, vol. 43, No. 7, pp. 611-617 (Abstract Only).
Nico Corporation Press Release, "NICO Corporation Gains Market Expansion after Multiple Published Clinical Articles Support Access Technology for Deep Brain Lesions," May 5, 2015, pp. 1-2.
Ding, D. et al., "Endoport-assisted microsurgical resection of cerebral cavernous malformations," J. Clin. Neurosci., Jun. 2015, vol. 22, No. 6, pp. 1025-1029 (Abstract Only).
Del Ray Medical Center Press Release, "Advanced Neuroscience Network Brings New Innovations in Neurosurgery to South Florida," May 13, 2015, pp. 1-6.
Final Office Action for U.S. Appl. No. 14/134,360, dated Jan. 12, 2016, 13 pages.
Notice of Allowance dated Mar. 11, 2016 for U.S. Appl. No. 14/134,360, 10 pages.
Recinos, et al. "Use of a minimally invasive tubular retraction system for deep-seated tumors in pediatric patients," Journal of Neurosurgery: Pediatrics, vol. 7, May 2011, pp. 516-521. 6 pages.
Non Final Office Action for U.S. Appl. No. 14/727,361, dated Jul. 14, 2016, 31 pages.
Non Final Office Action for U.S. Appl. No. 14/427,374, dated Jul. 22, 2016, 35 pages.
Notice of Allowance for U.S. Appl. No. 14/727,361, dated Sep. 21, 2016, 8 pages.
Shults, et al. "Neuro-Opthalmic Complications of Intracranial Catheters," Neurosurgery, vol. 33, No. 1, Jul. 1993, pp. 135-138. 4 pages.
Non Final Office Action for U.S. Appl. No. 15/004,332, dated Nov. 18, 2016, 26 pages.
Final Office Action for U.S. Appl. No. 14/727,374, dated Nov. 23, 2016, 14 pages.
Non Final Office Action for U.S. Appl. No. 14/711,305, dated Dec. 7, 2016, 42 pages.
International Preliminary Report on Patentability for International Application No. PCT/US2015/030528, dated Nov. 15, 2016, 7 pages.

(56) References Cited

OTHER PUBLICATIONS

Non Final Office Action for U.S. Appl. No. 15/004,332, dated Feb. 14, 2017, 12 pages.
Notice of Allownce for U.S. Appl. No. 14/727,374, dated Jan. 19, 2017, 9 pages.
Extended European Search Report for European Application No. 15793215.3, dated Mar. 24, 2017, 6 pages.
Notice of Allowance for U.S. Appl. No. 14/711,305, dated Apr. 18, 2017, 11 pages.
Notice of Allowance for U.S. Appl. No. 15/004,332, dated Jun. 14, 2017, 8 pages.
Notice of Allowance for U.S. Appl. No. 15/083,916, dated Jan. 30, 2018, 12 pages.
Notice of Allowance for U.S. Appl. No. 15/083,940, dated Jan. 22, 2018, 7 pages.
International Search Report for International Application No. PCT/US2017/060373, dated Jan. 23, 2018, 8 pages.
European Communcation pursuant to Article 94(3) for European Applicatin No. 15793215.3, dated Jan. 15, 2018, 4 pages.
Chinese Office Action for Application No. 201580031654.3, dated Sep. 30, 2017, 18 pages.
Non Final Office Action for U.S. Appl. No. 15/613,904, dated Oct. 5, 2018, 34 pages.
Notice of Allowance for U.S. Appl. No. 15/613,904, dated Feb. 8, 2019, 9 pages.
International Preliminary Report on Patentability for International Application No. PCT/US2017/060373, dated May 7, 2019, 8 pages.

\* cited by examiner

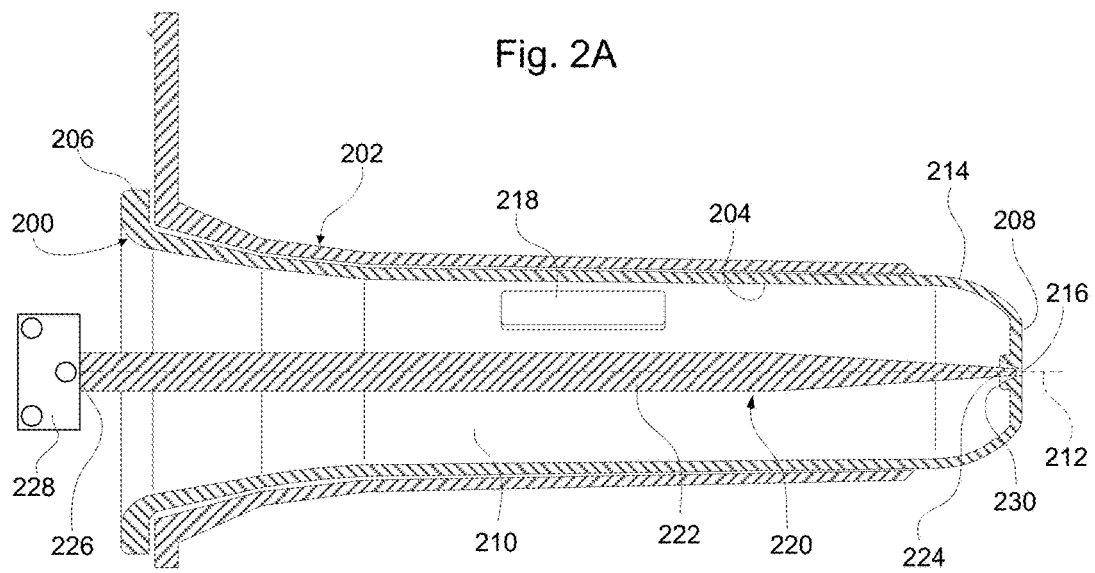
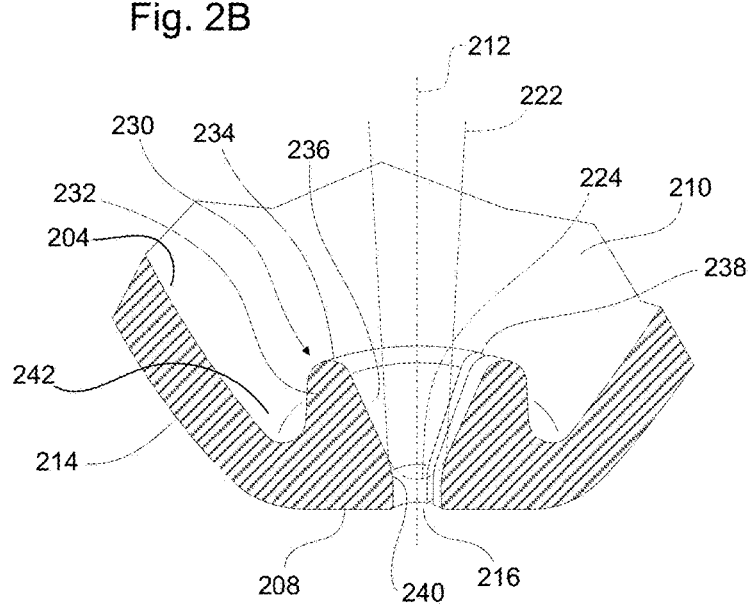

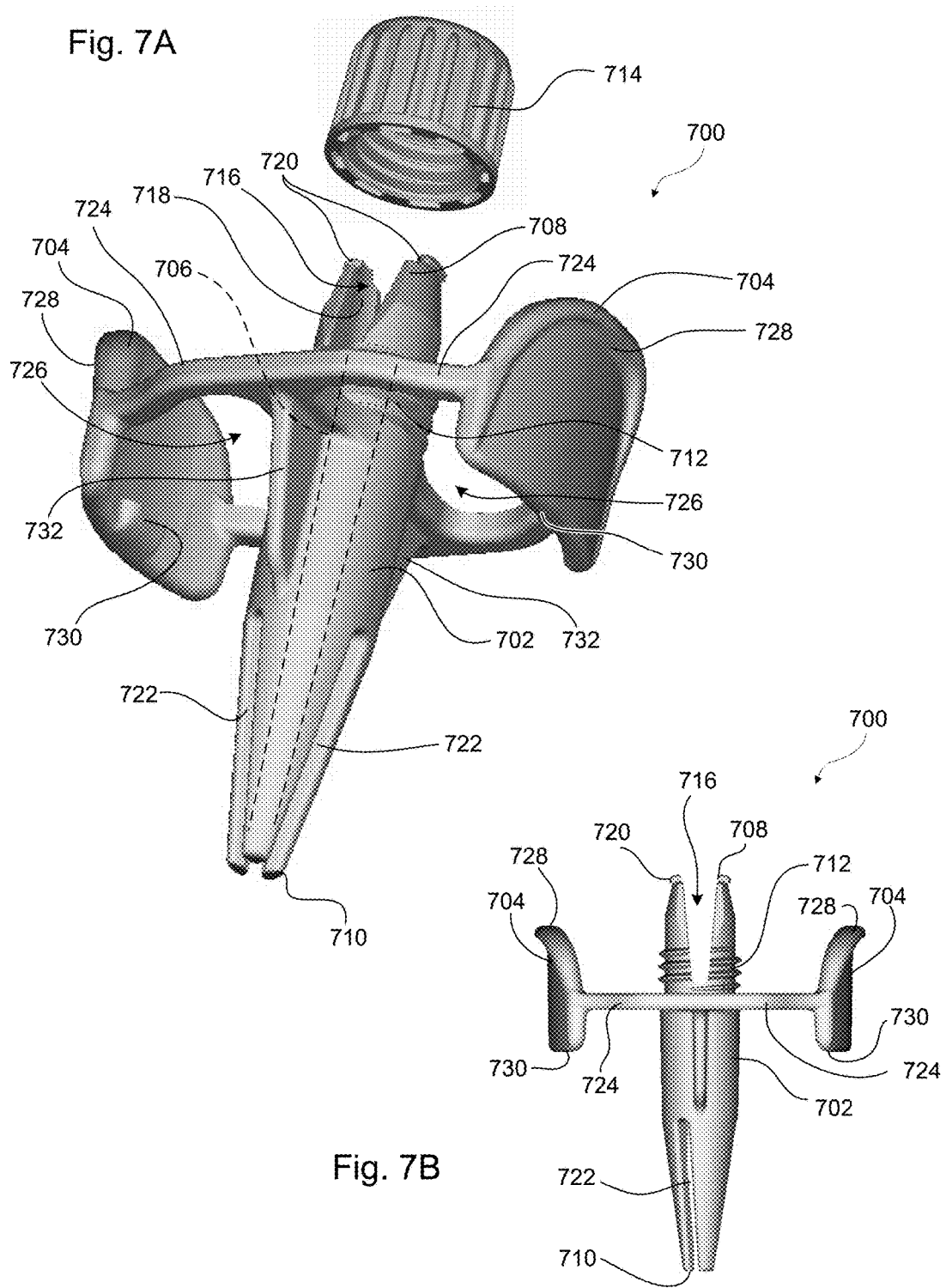

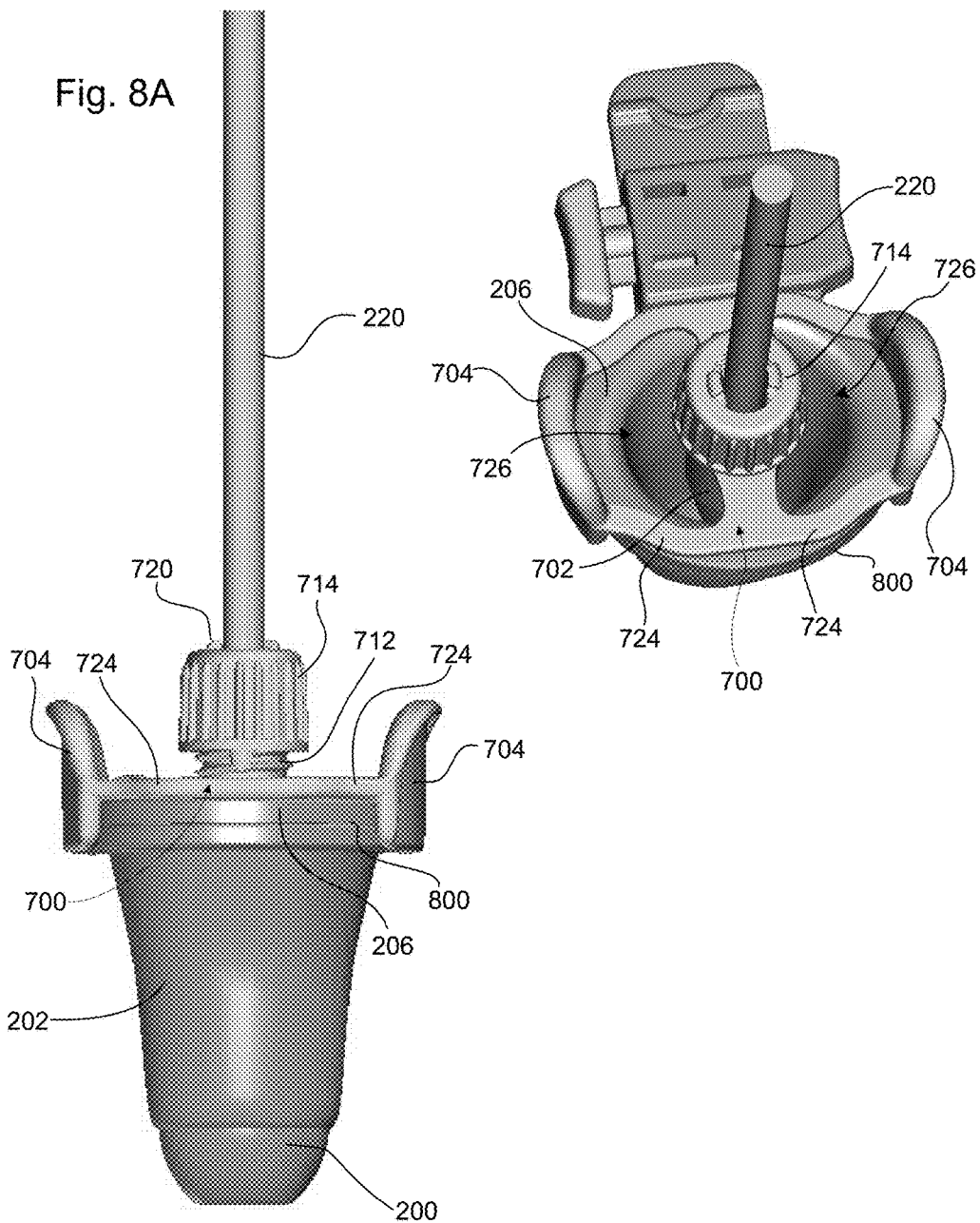

SURGICAL INTRODUCER WITH GUIDANCE SYSTEM RECEPTACLE

CROSS REFERENCE TO RELATED APPLICATIONS

This application claims priority to U.S. Provisional Application No. 62/418,507, entitled SURGICAL INTRODUCER WITH GUIDANCE SYSTEM RECEPTACLE, filed Nov. 7, 2016, the contents of which is incorporated fully herein by reference.

FIELD OF THE INVENTION

The present invention relates to delicate tissue surgical retractor systems for use in the brain or other tissue susceptible to retraction injury.

BACKGROUND

A variety of different devices have been used to retract delicate tissue during surgical procedures. One such device is illustrated in United States Patent Publication Number 2010/0010315, which is incorporated herein by reference. FIG. 1 of this publication illustrates a soft tissue retractor system having a hollow retractor 100, and an introducer 102 that is selectively inserted into the retractor 100. The retractor 100 and/or introducer 102 may include a handle 104 to facilitate manipulation and placement of the retractor system, and a lock to hold the introducer and retractor together. The handle 104 is configured to connect to a clamp 106, such as the standard surgical clamp 106 shown in FIG. 1. The device in FIG. 1 (with some modifications) is commercially sold as the "VBAS" device by Vycor Medical, Inc. of Boca Raton, Fla.

A retractor system such as shown in FIG. 1 is often used by inserting the introducer 102 into the retractor 100 and locking it in place, so the two can be moved and manipulated as a unit. The combined retractor system is inserted into the patient's body and moved to the surgery site, and then the introducer 102 is unlocked and removed to permit access to the site through the retractor 100. When the unit is in place (either before or after the introducer 102 is removed), the handle 104 may be locked to a clamp 106 to hold the retractor 100 in place. Surgeons using this retractor sometimes do not use a clamp to hold the retractor at the surgery site, and often manually manipulate the retractor to access different parts of the surgery site during the surgical procedure. The retractor system and the retractor may be manipulated by holding the proximal ends of the introducer or retractor or by holding the handle.

The device shown in FIG. 1 may have a transparent introducer 102 and/or retractor 100, and surgeons using such devices advantageously use the transparent introducer and retractor to observe the underlying tissue and to visually guide the unit to the surgery site. While it has been found that visual guidance by looking through the introducer 102 is very beneficial, it also has been found that some form of additional guidance or navigation may be desired in some cases. For example, in some cases, surgeons have used a probe or guide wire (a narrow elongated rod) to guide the movement of the retractor system. In such cases, the probe is advanced to the surgery site, and then the interlocked retractor system is slid over the probe until it reaches the surgery site. This is facilitated by the inclusion of a hole at the tip of the introducer that fits around the probe. If the hole through the tip of the introducer is absent, this method cannot be used. This type of system is described in United States Patent Publication Numbers 2008/0109026 and 2009/0048622, which are incorporated herein by reference. These references also show an alternative construction, in which the retractor is not locked to the introducer.

It has been found that some surgeons using the above procedure may use a probe that is integrated into a computer navigation system. For example, the probe may include a so-called "starburst" or the like, on the probe's proximal end (i.e., the end opposite the distal end that is inserted to the surgical site). This and other navigation systems are known in the art. For example, frameless navigation systems and other computerized guidance systems and methods are described in U.S. Publication No. 2001/0027271 (which is incorporated herein by reference in its entirety) and others, and are commercially available from companies such as Medtronic, Inc., Stryker, BrainLab, AG, and GE Healthcare. As used herein, "computerized guidance" encompasses any method of guiding a device to or at a surgical site that relies on computer visualization and/or control.

United States Patent Publication Number 2010/0010315 briefly notes the possibility of using stereotactic guidance or navigation in conjunction with a surgical retractor, but does not illustrate or describe this procedure or any apparatus for accomplishing this objective. Nevertheless, surgeons have been known to use a navigation probe "freehand" with a VBAS device such as shown in FIG. 1. In such cases, the surgeon holds the navigation probe in place within the introducer while advancing the unit towards the surgery site. The tip of the probe may be placed in or near an opening through the tip of the introducer, but the opening through the introducer may be somewhat larger than the probe tip and is oval, and does not hold the probe tip in any particular orientation. Such techniques can suffer from inaccuracy and displacement of the probe from the introducer tip, and it can be difficult to hold the probe in place. Also, in some cases the probe tip may extend partially through the introducer tip opening, which can risk damaging underlying tissue. However, freehand use can be helpful to allow occasional removal of the probe to provide an unobstructed view through the introducer of the underlying tissue.

While computerized surgical guidance systems are well-known, a number of limitations exist with respect to their use with retractor systems, and particularly with systems like those shown in FIG. 1. For example, while some surgeons use computerized guidance to direct a probe to the surgery site, and then slide the retractor system over the probe to the site, the movement of the retractor may be somewhat imprecise and the process can be unduly cumbersome. This method also is not available if the retractor system does not have a through-hole that fits over the probe (due either to the absence of a hole or a hole that is too small). In addition, the probe does not provide a view of the tissue through which it is advanced, so there is no visual means to perceive and avoid critical tissue (e.g., major blood vessels or nerves) when inserting a probe before inserting a retractor/introducer system. Also, the small-diameter probe may sever delicate tissue cells, such as grey or white brain matter, rather than moving the cells aside and passing between them as would be expected to happen when advancing the retractor system.

United States Patent Publication Number 2013/0066154, which is incorporated herein by reference, shows examples of systems for integrating a navigation probe into a surgical introducer. For example, FIGS. 1-6 of this publication show a navigation probe that is secured to the inside of a pre-existing introducer by resilient means, such as rubber plugs or O-rings. Another embodiment uses a slip fit (e.g., FIGS. 7-8), and still another embodiment uses an arm to hold the probe down inside the introducer (FIG. 9). Still other versions mount the navigation device outside the introducer, to an arm that is connected to the retractor assembly (FIGS. 10-11). While these systems may provide suitable performance, they also have certain potential shortcomings. For example, resilient plugs may slip in the presence of fluids and may be difficulty to disengaged to remove the navigation device during surgery, a slip fit requires careful monitoring to ensure proper positioning, an arm as shown in FIG. 9 to hold the probe in place requires the probe to be modified to include a surface against which the arm pushes, and locating the navigation device outside the introducer complicates the correlation between the navigation device and the tip of the introducer or retractor.

United States Patent Publication Number 2012/0071748, which is incorporated herein by reference, shows another example of a system for integrating a navigation probe into a surgical introducer. In this case, the probe is retained in a narrow channel through the introducer, and held in place with a threaded locking screw. The locking screw adds an additional potentially-removable part to the operating theater, and therefore this reference adds a separate retaining device (see FIG. 7B) to prevent the locking screw from being removed. The locking screw also can be relatively difficult to manipulate, particularly when wearing surgical gloves.

United States Patent Publication Number 2016/0015374, which is incorporated herein by reference, shows yet another example of a system for integrating a navigation probe into a surgical introducer. The device shown in this publication holds the probe in a tube-like sheath that extends distally into the introducer from the proximal open end of the introducer, and has a convenient single-throw clamp to lock the probe in place. This device also optionally includes a mechanism to indicate when the navigation probe is fully seated in the introducer. While this device is useful to ensure greater accuracy and registration between the introducer and the navigation probe, it may obstruct the surgeon's view to some degree, and may make frequent removal and reinstallation of the navigation probe somewhat cumbersome as compared to freehand use of the probe.

It has been found that there still remains a need to provide alternative apparatus and methods for coordinating the use of guidance systems with surgical introducers.

SUMMARY OF THE INVENTION

In one exemplary aspect, there is provided an introducer system for use with a navigation probe having a navigation element and a navigation probe shaft having a diameter and terminating at a distal probe tip. The introducer system includes a sidewall extending along a longitudinal axis and forming an introducer passage extending from a proximal introducer end to a distal introducer end, the sidewall being larger, in a lateral direction that is orthogonal to the longitudinal axis, than the navigation probe shaft diameter. The introducer also includes a probe receptacle located at the distal introducer end, the probe receptacle extending along the longitudinal axis within the introducer passage from a proximal receptacle end to a distal receptacle end, the probe receptacle having an inner surface having a first lateral size in the lateral direction at the proximal receptacle end and a second lateral size in the lateral direction at the distal receptacle end, the first lateral size being greater than the second lateral size. The inner surface is configured and dimensioned to receive the distal probe tip and restrict movement of the distal probe tip in the lateral direction, and the sidewall is configured and dimensioned to allow the navigation probe shaft to move in the lateral direction within the passage when the distal probe tip is positioned in the probe receptacle.

The sidewall may have an elliptical profile in the lateral direction, and the probe receptacle may have a circular profile in the lateral direction. The sidewall may have a profile in the lateral direction, and the probe receptacle may be located at the geometric center of the sidewall profile.

The inner surface may have a proximal portion adjacent the proximal receptacle end having a first angle relative to the longitudinal axis, and an intermediate portion located distally from the upper portion and having a second angle relative to the longitudinal axis, the second angle being less than the first angle. The first angle may be 20°-30° and the second angle may be 5°-15° degrees. The inner surface further may include a distal portion located distally from the intermediate portion forming at least a portion of a hemispherical surface.

The probe receptacle may have a distal receptacle opening passing through the distal receptacle end and forming a first fluid flow path between the inner surface and an exterior of the sidewall at the distal introducer end. The introducer also may include an introducer tip opening forming a second fluid flow path between the introducer passage and the exterior of the sidewall at the distal introducer end.

At least a portion of the probe receptacle may be spaced from the sidewall in the lateral direction by a gap. The probe receptacle may have at least one opening at a location between the receptacle proximal end and the receptacle distal end forming a fluid communication path between the inner surface and the gap.

The introducer may have an introducer tip opening forming a fluid flow path through the sidewall at the distal introducer end. At least a portion of the probe receptacle may be spaced from the sidewall in the lateral direction by a gap. At least one passage may be provided through an outer wall of the probe receptacle between the receptacle proximal end and the receptacle distal end, the at least one passage forming a fluid communication path between the introducer tip opening and the gap, the fluid communication path being configured to at least partially bypass the proximal receptacle end. The at least one passage may be a plurality of slots extending through the outer wall of the probe receptacle, each of the plurality of slots extending along the longitudinal axis from the proximal receptacle end to a portion of the sidewall located adjacent the distal receptacle end. The introducer may have at least one passage through the inner surface to the introducer tip opening, and the at least one passage may include one or more annular passages.

The probe receptacle may overlie the introducer tip opening as viewed along the longitudinal axis and the introducer may further include at least one fluid flow path that extends through the introducer tip opening without passing through the proximal receptacle end. The introducer may have one or more supports extending between the sidewall and the probe receptacle to suspend the probe receptacle adjacent the introducer tip opening. The one or more supports may be a plurality of ribs extending along the longitudinal axis. The distal receptacle end may be located within the introducer tip opening. At least part of the one or more supports may be located within the introducer tip opening. The probe receptacle may be smaller or larger in the lateral direction than the introducer tip opening.

The inner surface may be configured to hold the distal probe tip adjacent the distal introducer end. The inner surface may be configured to hold the distal probe tip within 1.0 mm, or within 0.5 mm, of the distal introducer end. The inner surface may be configured to hold at least four different navigation probes, each navigation probe having a distal probe tip having a geometric shape that is distinct from the other navigation probes, with each of the distal probe tips located, when fully installed in the probe receptacle, within 1.0 mm, or within 0.5 mm, of the distal introducer end.

At least a portion of the sidewall at the distal introducer end may be transparent and visible from the proximal introducer end when the navigation probe is installed within the introducer.

The introducer system may also include a probe retainer configured to selectively connect to the proximal introducer end. The probe retainer has a receiver configured to receive the navigation probe shaft when the probe retainer is attached to the proximal introducer end and thereby limit movement of the navigation probe shaft in the lateral direction.

In another exemplary embodiment, there is provided an introducer system for use with a navigation probe having a navigation element and a navigation probe shaft having a diameter and terminating at a distal probe tip. The introducer system has an introducer having a sidewall extending along a longitudinal axis and forming an introducer passage extending from a proximal introducer end to a distal introducer end, the sidewall being larger, in a lateral direction that is orthogonal to the longitudinal axis, than the navigation probe shaft diameter, and a probe receptacle located at the distal introducer end, the probe receptacle extending along the longitudinal axis within the introducer passage from a proximal receptacle end to a distal receptacle end, the probe receptacle having an inner surface having a first lateral size in the lateral direction at the proximal receptacle end and a second lateral size in the lateral direction at the distal receptacle end, the first lateral size being greater than the second lateral size. The introducer system also includes a probe retainer configured to selectively connect to the proximal introducer end. The probe retainer includes a receiver configured to receive the navigation probe shaft and limit movement of the navigation probe shaft in the lateral direction.

The probe retainer may have one or more clamps connected to the receiver and configured to selectively connect to the proximal introducer end. The one or more clamps may be two clamps, each clamp being connected to the receiver by a clamp arm having an arm opening therethrough, and each arm opening being aligned with the introducer passage to provide a visual path into the introducer passage. The receiver may have a lock to selectively hold the navigation probe shaft.

The foregoing summary of the invention provides a variety of exemplary embodiments that may be used in any suitable combination, and is not intended to impose any limitations upon the invention recited in the claims.

BRIEF DESCRIPTION OF THE DRAWINGS

A better understanding of the exemplary embodiments may be understood by reference to the attached drawings, in which like reference numbers designate like parts. The drawings are exemplary, and not intended to limit the claims in any way.

FIG. 2A is a cutaway side view of a first embodiment of an introducer having a guidance probe receptacle.

FIG. 2B is a cutaway side view of the distal tip of the embodiment of FIG. 2A, shown at a slight oblique angle.

FIGS. 7A-7B illustrate an embodiment of a centering device that may be used with embodiments of introducers.

FIGS. 8A-8B illustrate the embodiment of FIGS. 7A-7B in use.

DETAILED DESCRIPTION OF EMBODIMENTS

Embodiments of the invention may provide various features to supplement or advance the state of the art of surgical introducers and retractor systems. As used herein, the term "guidance system" is intended to include any system for assisting a surgeon with advancing the retractor system to the surgery site, and can include passive systems like guide wires, or active systems like navigation probes that are detected and tracked using a computerized telemetry system. The term "surgeon" includes anyone in the operation theater who might use or manipulate the introducer system. Active probes can be tracked by various techniques, including: optically tracking a "starburst" or other marker mounted on a portion of the probe that remains visible during the procedure; directly monitoring the probe's position using radiation imaging (e.g., X-ray) or magnetic imaging; physically connecting the probe to a frame of reference system to mechanically track the position of the probe; or other means or combinations of means, as known in the art. The terms "navigation" and "guidance" are used interchangeably herein. Embodiments also may be used with manual systems in which the surgeon moves the retractor system entirely by hand, or semi-automated or automated systems that operate under the surgeon's control or automatically advance the retractor system to the surgery site without the surgeon's intervention.

Figure 1:
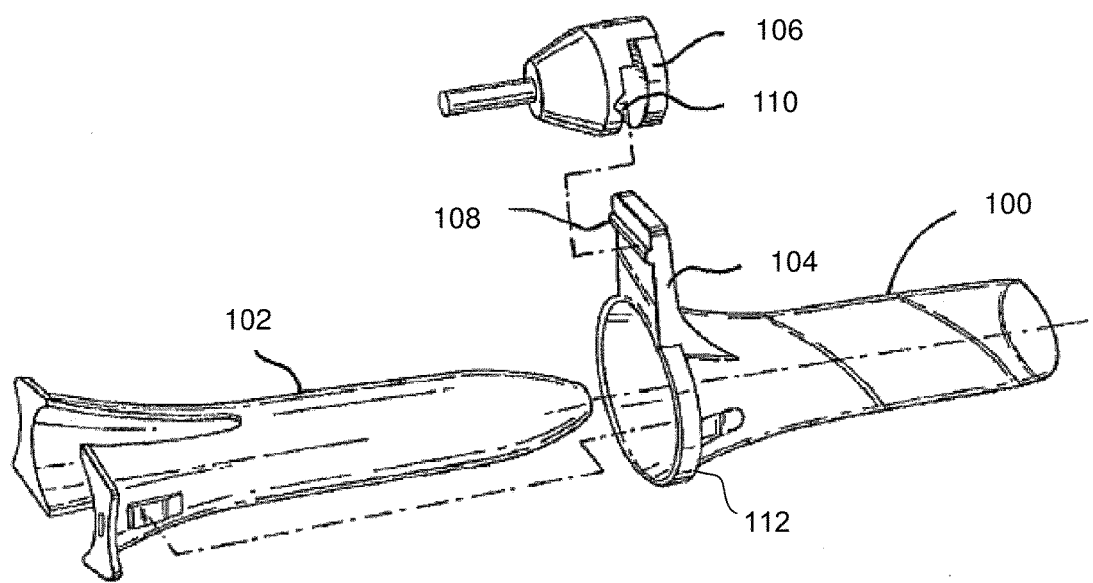
FIG. 1 is an example of a prior art delicate tissue retractor system.

Embodiments may be used with dedicated systems that are designed anew, or with preexisting systems. For example, embodiments may be used with systems like the one shown in FIG. 1, such as by supplementing, modifying or replacing the introducer 102, or with other introducer assemblies, as will be appreciated by persons or ordinary skill in the art. The embodiments described herein may be used with a retractor 100 as shown in FIG. 1, or in other retractors. It will be readily appreciated that the shape of the introducer can be modified to fit into any conventional retractor, and the introducer also may be modified to connect to the retractor (if necessary or desired) using any suitable clamp or other engagement mechanism. For example, embodiments may be used with small-scale versions of introducers like the one shown in FIG. 1, in which the embodiment optionally may be scaled down to allow visibility into the retractor, but providing such visibility is not required in all embodiments.

The exemplary embodiments described herein are directed towards introducers for use in neurosurgery or other operations in and around the brain or skull. However, uses in other parts of the body are also possible.

FIG. 2A shows an exemplary embodiment of an introducer 200 that is configured to be releasably retained inside a retractor 202 such as retractor 100 of FIG. 1. The introducer 200 comprises a sidewall 204 that extends from a proximal introducer end 206 to a distal introducer end 208. As used herein, "proximal" refers to the end that generally faces the surgeon in use, and "distal" refers to the end that is located towards or inserted into the patient. When connected together, the proximal introducer end 206 may be located at or near a proximal retractor end, and the distal introducer end 208 extends beyond a distal retractor end. The retractor 202 preferably comprises a hollow tubular retractor passage extending along a longitudinal axis from a proximal retractor end to a distal retractor end, and is dimensioned to allow surgical procedures to be undertaken therethrough.

The introducer sidewall 204 forms an introducer passage 210 that extends along a longitudinal axis 212 extending from the proximal introducer end 206 to the distal introducer end 208. When assembled with the retractor 202, a distal tip portion 214 of the introducer 200 extends beyond the distal end of the retractor 202. Together, the distal tip portion 214 and the retractor 202 form a generally smooth and continuous surface for gently displacing brain tissue or the like as the assembly is advanced into the body. The distal tip portion 214 preferably is tapered with a rounded (such as shown) or conical shape. A tip opening 216 may be provided at or near the distal introducer end 208, as discussed in more detail below. A lock (see, e.g., FIG. 1) may be provided to selectively hold the introducer 200 to the retractor 202.

The sidewall 204 preferably comprises a continuous wall surface such that the passage 210 has a closed outer perimeter, such as shown in FIG. 1. This can help prevent unwanted entry of body fluids and provide a smooth continuous surface for viewing through the sidewall 204 (if it is transparent) and for guiding instruments down the length of the passage 210 without risk of displacement. However, one or more openings 218 may be provided in the sidewall 204 in alternative embodiments.

The introducer sidewall 204 may have any suitable cross-sectional profile (i.e., profile in a plane orthogonal to the longitudinal axis 212). For example, the sidewall 204 may be circular, elliptical, oval or otherwise generally curved (i.e., comprised entirely of curved surfaces and/or very short straight surfaces that effectively simulate a smoothly-curved shape). If desired, the cross-section may include one or more rectilinear segments (e.g., a D-shape), or may be entirely rectilinear (e.g., a square or triangular shape). The sidewall profile also may taper to be larger at the proximal end than at the distal end, and preferably reduces at least slightly in size as it approaches the distal introducer end 208. The outer surface of the sidewall 204 may be shaped to match the shape of a corresponding inner wall of the retractor 202, but this is not strictly required. The introducer sidewall 204 also preferably has a generally consistent wall thickness along its length, which can facilitate manufacturing and provide a more suitable optical path for viewing through the sidewall 204. It will be understood that cross-sectional shape of the passage 210 will be defined by the shape of the sidewall 204, and therefore the foregoing discussion about the shapes of the sidewall 204 applies also the shape of the passage 210.

The introducer 200 preferably is transparent at least at the distal end 206, and more preferably at the distal tip portion 214, and more preferably along most or the full length of the sidewall 202. The transparent portion allows the surgeon to visualize underlying tissue while advancing the introducer 200 through brain tissue or the like, which can provide significant benefits during surgery. However, in alternative embodiments, the introducer 200 may be opaque. Suitable materials for the introducer 200 include polycarbonate and other kinds of plastic, metals such as aluminum, stainless steel or titanium, glass or ceramic, or other materials that are biocompatible or that can be treated via coatings or the like to be biocompatible.

The passage 210 is sized to accommodate a navigation probe 220. The probe 220 comprises a shaft 222 that extends from a distal probe tip 224 to a proximal probe end 226. The probe 220 includes a navigation element 228 that is operatively associated with a navigation system to track the position of the probe 220 and convey this information to the surgeon during the course of surgery.

The navigation element 228 may comprise, for example, an optical array (e.g. three or more lights or reflectors in a predetermined physical pattern) that provides a three-dimensional registration of the position of the probe tip 224 when viewed by a corresponding navigation camera system. Such an array may be mounted to the proximal probe end 226 or elsewhere where it can be viewed by the navigation cameras. The need for a line-of-sight between the optical array and the cameras is likely to require the navigation element 228 to be positioned outside the introducer 200. Alternatively, the navigation element 228 may comprise a magnetic element that can be tracked by a corresponding magnetic tracking system. In this case, it may not be necessary to position the navigation element 228 outside the introducer 200. Other alternatives of navigation elements 228 will be apparent to persons of ordinary skill in the art in view of the present disclosure. Examples of navigation probes 220 and corresponding tracking systems are provided by Stryker Navigation of Kalamazoo, Mich., U.S.A.; Brainlab AG of Feldkirchen, Germany; Synaptive Medical of Toronto, Ontario; and Medtronic of Minneapolis, Minn., U.S.A.

The introducer passage 210 is significantly larger in the lateral direction (i.e., perpendicular to the longitudinal axis 212) than the probe shaft 222. This may allow the surgeon to visualize down the length of the passage 210 without her vision being unduly obstructed by the probe 220. This also may allow the surgeon to insert other instruments such as an endoscope or aspiration tube into the passage 210 while the probe 220 remains in place, and so on. As a consequence of their disparate relative sizes, the sidewall 204 does not hold the navigation probe shaft 222 against lateral movement within the passage 210. It expected that some lateral movement of the probe shaft 222 within the passage 210 will not critically affect proper navigation, but it is believed to be more important to assure continuous proper registration between the distal probe tip 224 and a fixed location at the distal introducer end 208. For example, maintaining the probe tip 224 with little or no deviation from the geometric center of the introducer profile at the distal introducer end 208 is expected to provide sufficient registration for accurate navigation, even if the proximal end of the shaft 222 might move laterally within the passage 210.

In the embodiment of FIGS. 2A and 2B, the probe tip 224 is maintained in registration with the distal introducer end 208 by a probe receptacle 230. The probe receptacle 230 preferably is located at the geometric center of the introducer profile at the distal introducer end 208 (e.g., the geometric center of the ellipse if the distal introducer end 208 is elliptical), but this is not strictly required in all embodiments. For example, the receptacle 230 may be offset from the introducer's central axis.

The probe receptacle 230, in this embodiment, comprises a generally circular receptacle wall 232 having an inner surface 236 that extends within the passage 210 from a distal receptacle end 240 to a proximal receptacle end 234. The inner surface 236 tapers from a relatively large diameter at the proximal receptacle end 234 to a relatively small diameter at a distal receptacle end 240. The distal receptacle end may be located at or near the distal introducer tip 208. The receptacle wall 232 is sized to restrict the distal probe tip 224 from moving laterally beyond a predefined range of movement. For example, the receptacle wall 232 may restrict movement of the probe tip 224 to a range of less than 1 millimeter ("mm") in the lateral direction, or more preferably it may be sized to restrict any movement in the lateral direction.

The diameter of the proximal receptacle end 234 may have any size, but preferably is not so large as to significantly obstruct vision through the introducer 200, and not so small that it is overly difficult to position the probe tip 224 within the receptacle 230 during surgery. The receptacle wall's tapered surface 236 helps guide the probe tip 224 to the proper location within the receptacle 230, and the surface 236 may have a conical or curved profile as viewed from the lateral direction. The surface 236 also may have a region with a shape specifically selected to match the shape of the probe tip 224. For example, if the probe tip 224 is hemispherical, all or a portion of the surface 236 may have a matching shape. As another example, if the probe tip 224 is cylindrical (or has a hemispherical tip with a cylindrical body immediately adjacent the tip), a distal portion of the surface 236 may have a matching cylindrical shape. Other alternatives will be apparent to persons of ordinary skill in the art in view of the present disclosure.

The receptacle wall 232 also may be shaped and sized to hold the probe tip 224 in close proximity to the distal introducer end 208. For example the distance from the distal introducer end 208 to the probe tip, as measured along the longitudinal axis 212, preferably is less than 5.0 mm, and more preferably less than 1.0 mm, and most preferably 0.5 mm or less. Where the probe tip 224 is at 1.0 mm or less from the distal introducer end 208 it may not be necessary to attempt to correct for this amount of displacement for purposes of navigating into the brain tissue, as this is expected to be within the normal amount of deviation of brain tissue movement within the skull. It is preferred, but not strictly required, that the probe tip 224 does not protrude beyond the distal introducer end 208.

The introducer tip opening 216 (if one is provided) may be located within the probe receptacle 230 at the end of the receptacle wall 232, such as shown in FIG. 2B. Alternatively, the introducer tip opening 216 may be located elsewhere in the distal introducer end 208 at a location outside the receptacle 230. The probe receptacle 230 also may include one or more openings forming flow passages 238 to allow fluid to bypass the receptacle wall 232; this feature can help ensure proper drainage of fluids that might otherwise accumulate at the distal end of the passage 210 at locations between the proximal receptacle end 234 and the sidewall 204. More specifically, a gap 242 may be provided between an outer wall 244 of the probe receptacle 230 and the introducer sidewall 204, and fluid may accumulate in this gap 242 under some circumstances. The flow passages 238 are provided to allow fluid to exit the gap 242.

In use, the surgeon assembles the introducer 200 and retractor 202 together, places the probe tip 224 into the receptacle 230, and uses computer-aided navigation provided by the probe 220 to guide the assembly to the surgery site. During navigation, the probe 220 indicates the position of the distal introducer end 208 relative to the underlying tissue via a computer screen overlay of a representation of the probe and a representation of the tissue. Throughout the process, the surgeon preferably can inspect the tissue through transparent walls of the introducer 200 and retractor 202, and can periodically remove the probe 220 as necessary to obtain a better visual image or to perform intermediate procedures such as suctioning fluid and the like.

Figure 3A:
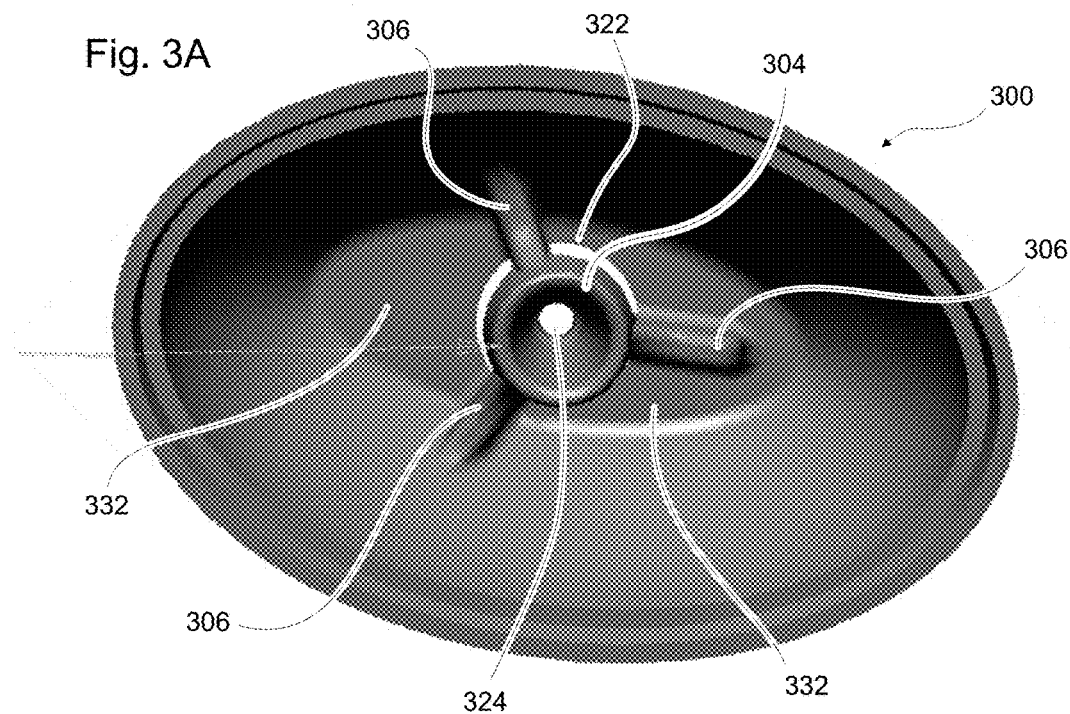
FIG. 3A illustrates a distal tip of another embodiment of an introducer having a guidance probe receptacle, as viewed from inside the introducer.
Figure 3B:
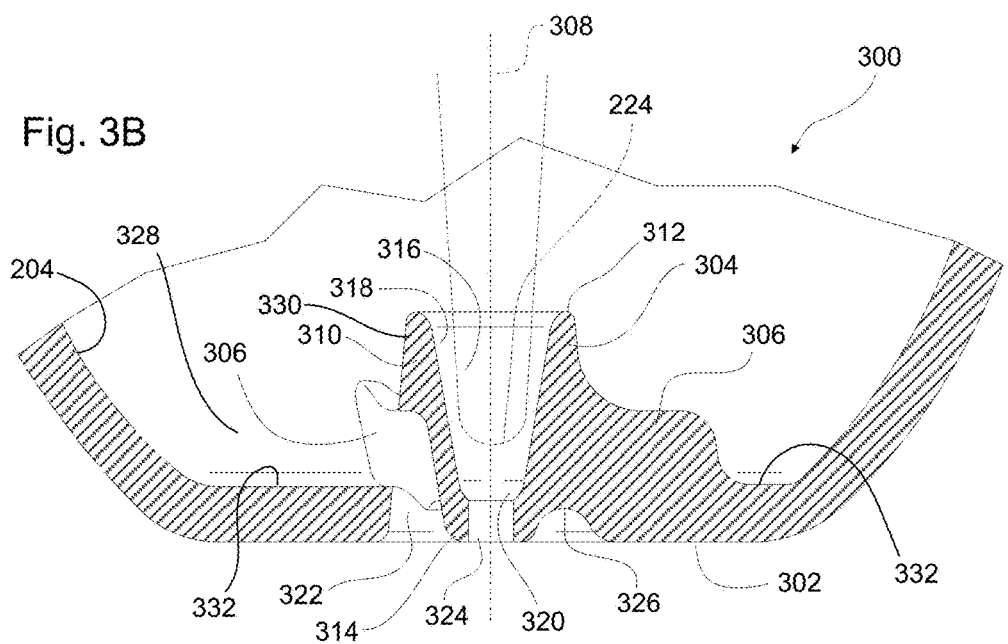
FIG. 3B is a cutaway side view of the distal tip of the embodiment of FIG. 3A.

FIGS. 3A and 3B illustrate another embodiment of an introducer 300. For simplicity, only the portion of the introducer 300 located near the distal introducer end 302 is shown in these illustrations, and it will be understood that other features of the introducer 300 such as the remainder of the internal passage and other features described previously herein will be connected to the illustrated portion. In this embodiment, introducer 300 has a probe receptacle 304 that is suspended within the introducer 300 by a number of supports 306.

The probe receptacle 304 may be located on the introducer's centerline, which is parallel to the introducer's longitudinal axis 308, but other locations are possible. The probe receptacle 304 preferably comprises a receptacle wall 310 (which is circular, but can have other shapes) that extends from a proximal receptacle end 312 to a distal receptacle end 314. The receptacle wall 310 has an inner surface 316 that tapers from a relatively large size at the proximal receptacle end 312 to a relatively small size at the distal receptacle end 314. The inner surface 316 is sized and shaped to retain the distal probe tip 224 to prevent the probe tip 224 from moving laterally. For example, FIG. 3B shows the probe tip 224 at a position shortly before it fully seats in the probe receptacle 304, to more clearly show that the tapered inner surface 316 transitions from a linearly tapering proximal surface portion 318 to a distal surface portion 320 that is shaped to match the hemispherical shape of the probe tip 224. When fully seated, the probe tip 224 abuts the distal surface portion 320 in something like a ball-and-socket arrangement, with the semi-hemispherical surface of the distal surface portion 320 cupping and closely conforming to the hemispherical probe tip 224. In other embodiments, the inner surface 316 may have other shapes to accommodate different shapes and sizes of probe tip 224. For example, a simple conical shape can accommodate different probes having various tip diameters.

The supports 306 are formed as planar ribs that radiate outward from the introducer's centerline, and extend in parallel with the longitudinal axis 308. In alternative embodiments, the supports 306 may be replaced by other shapes, such as blocks, pillars, and so on.

The probe receptacle 304 may be positioned adjacent to an introducer tip opening 322 that passes through the distal introducer end 302. The introducer tip opening 322 and probe receptacle 304 are positioned such that fluid located in a gap 328 between the probe receptacle's outer wall 330 and the sidewall 204 can pass through the introducer tip opening 322 without passing through the probe receptacle 304. Thus, fluid can flow through the introducer tip opening 322 even when the probe tip 224 is installed within the probe receptacle 304. The probe receptacle 304 also may include a distal receptacle opening 324 passing thorough the distal receptacle end 314, which provides an additional flow path when the probe is not installed in the probe receptacle 304 and prevents fluid from pooling in the probe receptacle 304.

In the illustrated embodiment, the distal receptacle end 314 extends into the introducer tip opening 322, such that it lies at or near the plane of the distal introducer end 302. Thus, the introducer tip opening 322 is formed as an annular passage that surrounds the probe receptacle 304, and the supports 306 bridge the gap between the distal introducer end 302 and the probe receptacle 304. The supports 306 may include arched voids 326 to help reduce any disruption in the flow through the introducer tip opening 322 that the supports 306 might otherwise cause.

The placement of the distal receptacle end 314 within the introducer tip opening 322 can place the probe tip 224 as close as possible to the distal introducer end 302. This simplifies the registration between the probe 220 and the introducer 300 because there is very little offset between their distal ends. However, this arrangement is not required in all embodiments. For example, the probe receptacle 304 may be moved further in the proximal direction (i.e., back into the introducer passage) to allow more fluid flow capacity through the introducer tip opening 322, to make the introducer tip opening 322 smaller, and for other reasons. If the offset between the probe tip 224 and the distal introducer end 302 is significant, the computer system associated with the probe 220 can be programmed to account for this offset when indicating the position of the introducer 300 to the surgeon, as known in the art.

The receptacle 304 is preferably positioned and sized such that at least a portion of the introducer sidewall 204 at the distal introducer end 302 is visible to the surgeon while the probe tip 224 is installed in the receptacle 304. For example, a pair of transparent faces 332 of the sidewall 204 (which may be flat as shown or curved) may be visible around the receptacle 304 and probe 220. The surgeon can visually inspect the underlying tissue even while the probe 220 is in place, and can move the probe shaft 222 around within the passage 210 to alter her view without displacing the probe tip 224 from the receptacle 304.

Figure 4A:
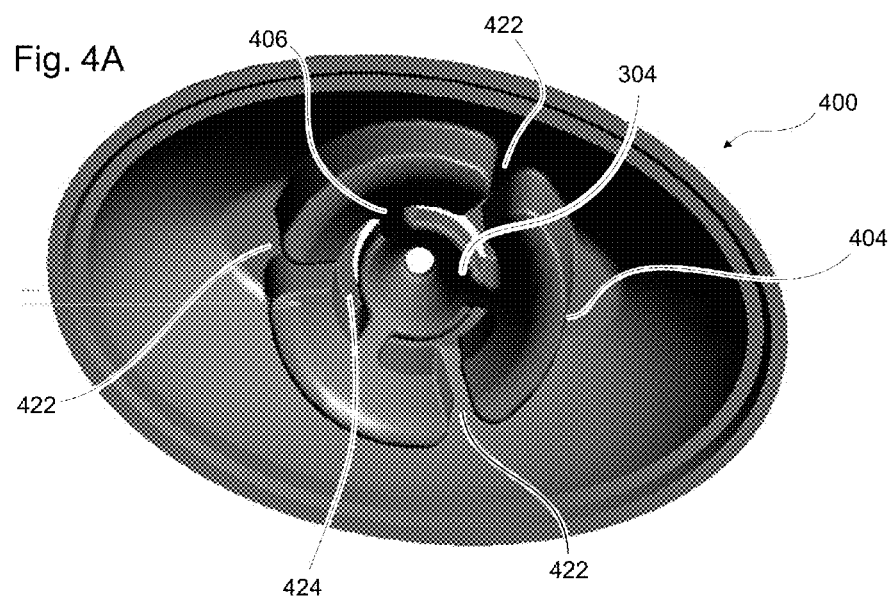
FIG. 4A illustrates a distal tip of another embodiment of an introducer having a guidance probe receptacle, as viewed from inside the introducer.
Figure 4B:
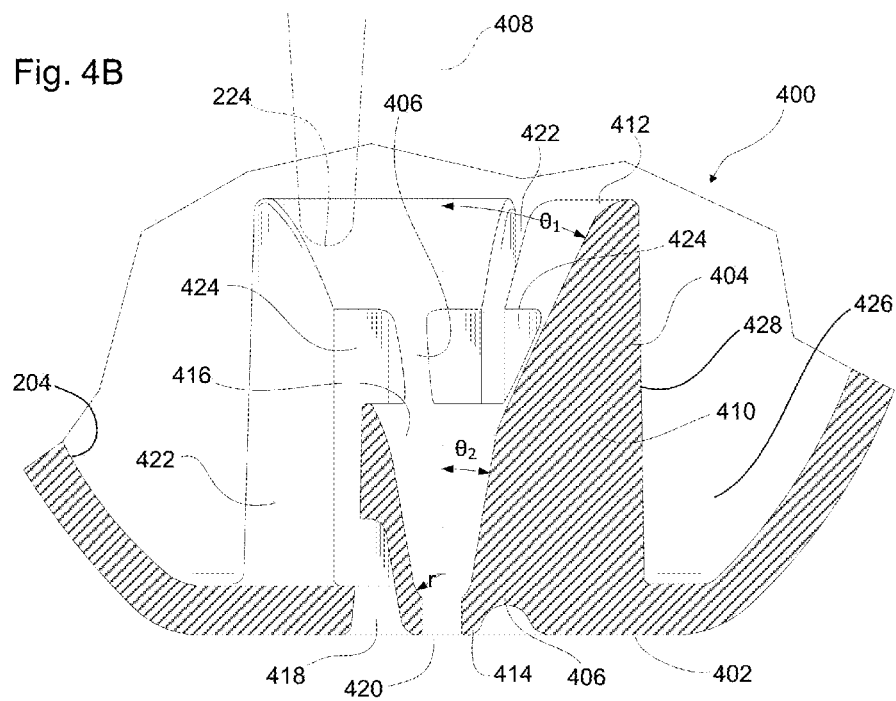
FIG. 4B is a cutaway side view of the distal tip of the embodiment of FIG. 4A.

FIGS. 4A and 4B illustrate another embodiment of an introducer 400. As with FIGS. 3A and 3B, only the region of the introducer 400 adjacent the distal introducer end 402 is shown. It will be understood that other features of the introducer 400 such as the remainder of the internal passage and other features described previously herein will be connected to the illustrated portion. In this embodiment, the introducer 400 has a probe receptacle 404 that includes a portion that is suspended within the introducer 400 by a number of supports 406. The probe receptacle 404 may be located on the introducer's centerline, which is parallel to the introducer's longitudinal axis 408, but other locations are possible.

The probe receptacle 404 preferably comprises a receptacle wall 410 (which is circular, but can have other shapes) that extends from a proximal receptacle end 412 to a distal receptacle end 414. The receptacle wall 410 has an inner surface 416 that tapers from a relatively large size at the proximal receptacle end 412 to a relatively small size at the distal receptacle end 414. The inner surface 416 is sized and shaped to retain the distal probe tip 224 to prevent the probe tip 224 from moving laterally when the probe tip 224 is fully seated in the probe receptacle 404. The inner surface 416 may be similar in construction to the probe receptacle 304 described in relation to FIGS. 3A and 3B, or have other shapes configured to retain the probe tip 224. For example, the inner surface 416 may comprise a proximal portion adjacent the proximal receptacle end 412 having a first angle $\theta_1$ relative to the longitudinal axis 408 in the range of 20°-30° (e.g., 25°), an intermediate portion located distally from the upper portion having a second angle $\theta_2$ relative to the longitudinal axis 408 in the range of 5°-15° degrees (e.g., 10°), and a distal portion located distally from the intermediate portion having a hemispherical or semi-hemispherical shape having a radius r in the range of 0.3-0.8 mm. This arrangement is expected to provide simple and repeatable installation of the probe tip 224 into the receptacle 404, and provide a distinct feel to indicate when the probe tip 224 is fully seated.

The probe receptacle 404 is positioned adjacent to an introducer tip opening 418 that passes through the distal introducer end 402. The introducer tip opening 418 and probe receptacle 404 are positioned such that fluid can pass through the introducer tip opening 418 without passing through the proximal receptacle end 412. This allows fluid located in a gap 426 between the probe receptacle's outer wall 428 and the introducer sidewall 204 to flow through the introducer tip opening 418 when the probe tip 224 is installed within the probe receptacle 404. In the shown embodiment, the outer wall 428 is shown being spaced from the sidewall 204 around its entire perimeter, but it will be appreciated that the outer wall 428 may merge with the sidewall 204 at some locations (such as when the introducer profile is a narrow ellipse or oval, and the receptacle 404 has a circular profile).

The probe receptacle 404 also may include a distal receptacle opening 420 passing thorough the distal receptacle end 414, to provide an additional flow path when the probe is not installed in the probe receptacle 404, and prevent fluid from pooling in the probe receptacle 404. The distal receptacle end 414 may extend into the introducer tip opening 418, such that it lies at or near the plane of the distal introducer end 402. In this case, the introducer tip opening 418 may be formed as an annular passage that surrounds the probe receptacle 404 with the supports 406 bridging the gap between the distal introducer end 402 and the probe receptacle 404. The supports 406 may include arched voids to help reduce any disruption in the flow through the introducer tip opening 418 that the supports 406 might otherwise cause. As with the embodiment of FIGS. 3A and 3B, locating the distal receptacle end 414 within the introducer tip opening 418 can place the probe tip 224 as close as possible to the distal introducer end 402. However, this arrangement is not required in all embodiments.

In this embodiment, the proximal receptacle end 412 is larger in the lateral direction (i.e., perpendicular to the longitudinal axis 408) than the introducer tip opening 418. This provides a relatively large probe receptacle 404 to help guide the probe 220 into place, while keeping the size of the introducer tip opening 418 relatively small to help prevent the possibility of brain tissue or other delicate tissue being damaged by being forced into or cut by the edges of the introducer tip opening 418. FIG. 4B shows how this configuration helps guide the probe tip 224 into the probe receptacle 404, even when it starts at a location that is significantly offset from the probe receptacle's centerline (which, in this example, is collinear with the geometric center of the introducer 400).

Where the proximal receptacle end 412 is larger than the introducer tip opening 418, it may be particularly favorable to provide additional provisions for assuring suitable flow through the introducer tip opening 418. To this end, the probe receptacle 404 may include one or more (preferably three) openings at a location between the proximal receptacle end 412 and the distal receptacle end 414 to allow fluid to flow to the introducer tip opening 418 without passing through the proximal receptacle end 412. Such openings may be, for example, slots 422 extending inward from the outer surface of the probe receptacle 404 to the introducer tip opening 418. These slots 422 allow fluid to drain from the most distal parts of the introducer passage to prevent pooling around the outer perimeter of the probe receptacle 404 at the distal end of the introducer. The slots 422 in the shown embodiment extend in the longitudinal direction from the proximal receptacle end 412 to a portion of the sidewall 204 located adjacent the distal receptacle end 414, but other embodiments may have slots having different lengths in the longitudinal direction.

Each slot 422 may terminate at its inner end at an annular passage 424 that overlies the introducer tip opening 418. The annular passage 424 passes through the inner surface 416 of the receptacle 424 and extends to the introducer tip opening 418, and is expected to help redistribute fluids passing through the introducer tip opening 418 into a more uniform and less restricted flow. The supports 406 bridge and interrupt the annular passage 424 to join the proximal receptacle end 412 to the distal receptacle end 414 and to suspend the distal receptacle end 414 at the introducer tip opening 418. The slots 422 and annular passage 424 are sized to prevent the probe tip 224 from entering them (e.g., by having a 0.5 mm maximum width if the smallest probe tip 224 to be used is 0.8 mm or larger).

As with the other embodiments, the receptacle 404 is preferably positioned and sized such that a transparent portion of the introducer sidewall 204 at the distal introducer end 402 is visible to the surgeon while the probe tip 224 is installed in the receptacle 404, to allow visualization of the underlying tissue while the probe 220 is in place.

FIGS. 5A through 5D illustrate another embodiment of an introducer 500, of which only the region of the introducer 500 adjacent the distal introducer end 502 is shown. As with the previous embodiments, it will be understood that other features of the introducer 500 will be connected to the illustrated portion. In this embodiment, the introducer 500 has a probe receptacle 504 having primary supports 506 joining a proximal receptacle end 508 to a distal receptacle end 510. The distal receptacle end 510 is adjacent (and preferably within) an introducer tip opening 512. The proximal receptacle end 508 is larger, in a direction perpendicular to the longitudinal axis 514 of the introducer 500, than the introducer tip opening 512. The structure of this probe receptacle 504 is similar to the one illustrated in FIGS. 4A and 4B, and can include the same variations and features (e.g., a distal receptacle opening, etc.). The description of FIGS. 4A and 4B applies equally to the embodiment of FIGS. 5A-5D.

Figure 5A:
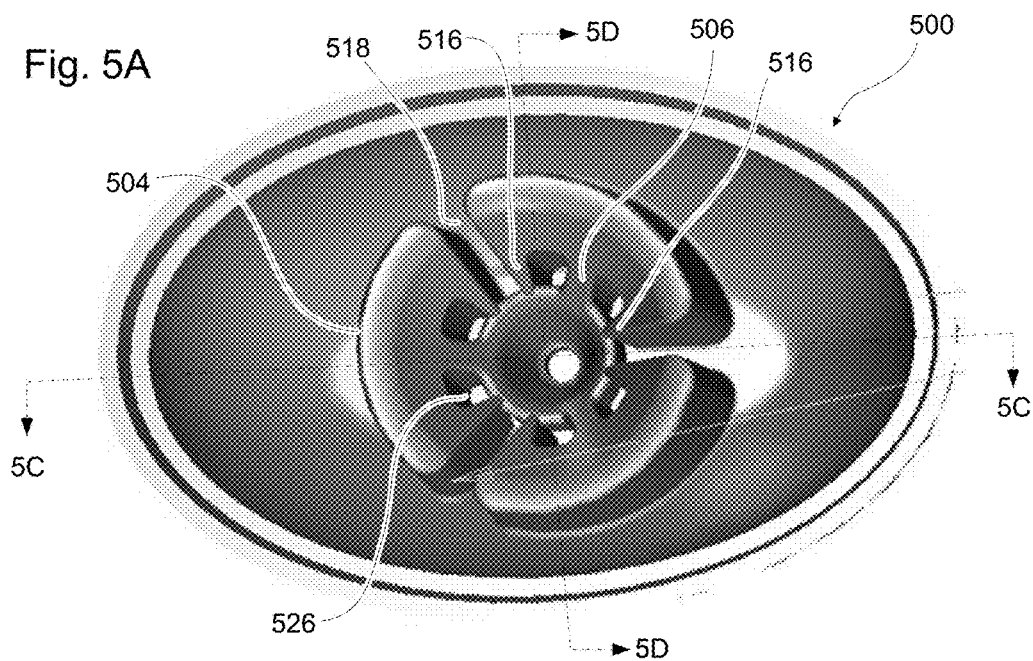
FIG. 5A illustrates a distal tip of another embodiment of an introducer having a guidance probe receptacle, as viewed from inside the introducer.
Figure 5B:
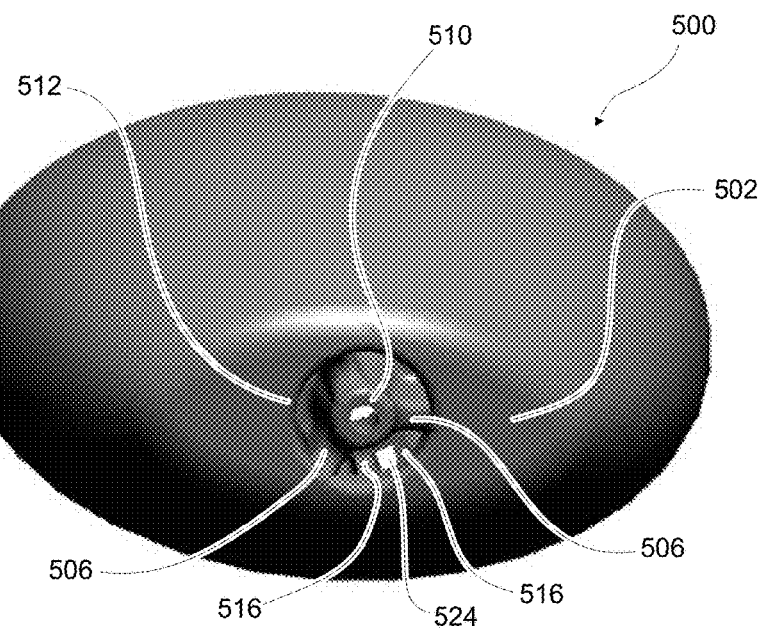
FIG. 5B illustrates the embodiment of FIG. 5A, as viewed from outside the introducer.
Figure 5C:
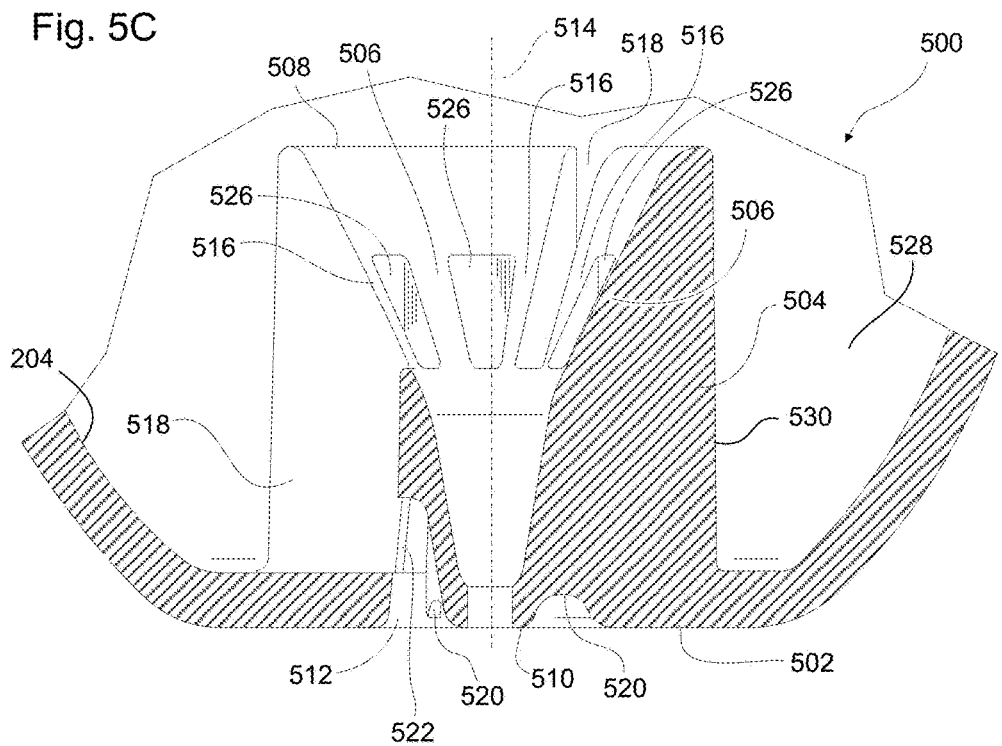
FIG. 5C is a cutaway side view of the distal tip of the embodiment of FIG. 5A, as shown along line 5C-5C.
Figure 5D:
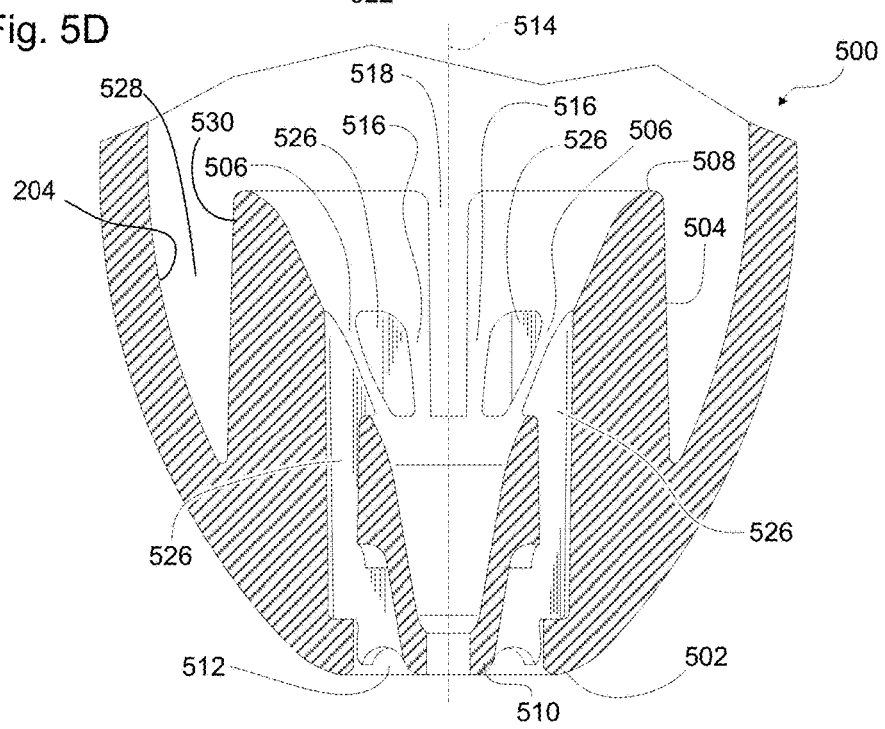
FIG. 5D is a cutaway side view of the distal tip of the embodiment of FIG. 5A, as shown along line 5D-5D.
Figure 6A:
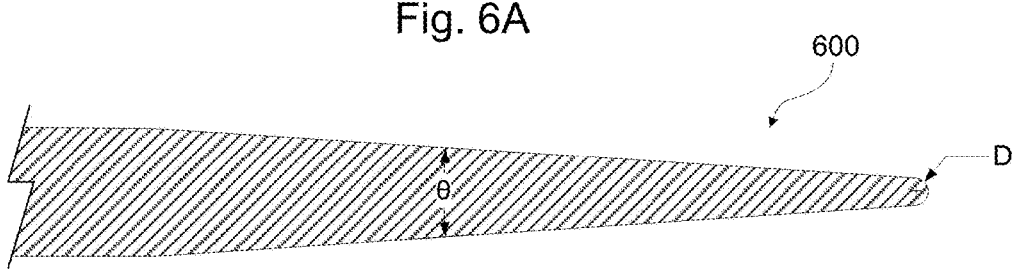
FIGS. 6A-6D are cross-sectional side views of the distal tips of four different navigation probes.
Figure 6B:
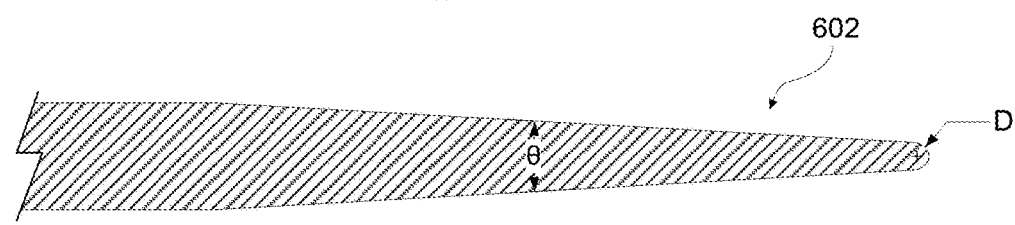
Figure 6C:
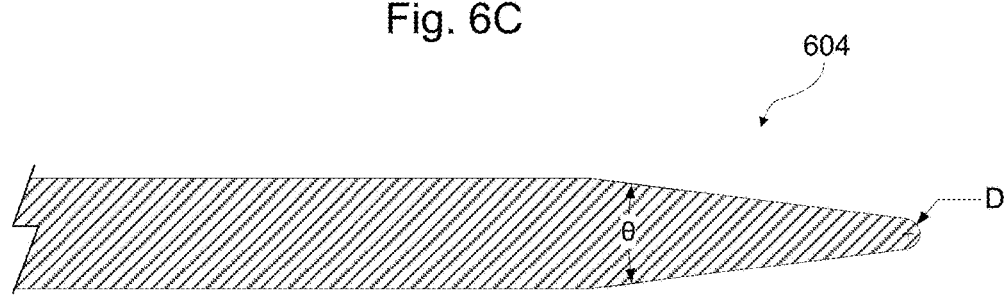
Figure 6D:
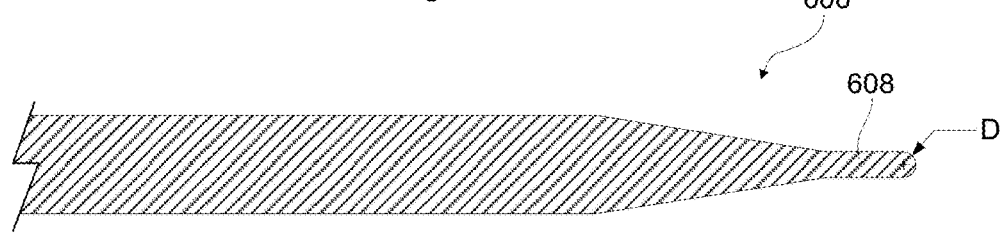

The embodiment of FIGS. 5A-5D differs from FIGS. 4A and 4B in that secondary supports 516 joining the proximal receptacle end 508 to the distal receptacle end 510 are provided on either side of each slot 518. The secondary supports 516 preferably have larger voids at their distal ends to provide a more continuous flow passage adjacent the introducer tip opening 512. For example, the primary supports 506 may be connected to the distal receptacle end 510 by ribs 520 having a lower end located within or near the introducer tip opening 512, while the secondary supports 516 are connected to the distal receptacle end 510 by ribs 522 that are spaced above the introducer tip opening 512, such as best shown in FIG. 5C. This arrangement provides additional structures to support the distal receptacle end 510 and to prevent a surgeon from lodging the probe tip 224 in the slots 518 or the gaps between the proximal receptacle end 508 and the distal receptacle end 510, while still providing an annular passage 524 (FIG. 5B) (which may be interrupted at some locations by the primary support ribs 520) at the introducer tip opening 512 to allow relatively free flow therethrough. Openings 526, located between the secondary supports 516 and primary supports 506, provide flow passages that pass through the inner surface of the probe receptacle 504 and extend along the longitudinal axis 514 to the introducer tip opening 512, to allow vertical fluid flow at various locations. As with the previous embodiments, fluid located in a gap 528 between the probe receptacle's outer wall 530 and the introducer sidewall 204 can flow through the introduced tip opening 512 without having to pass through the proximal introducer end 508, which helps reduce any flow restriction that might be caused by the probe tip 224.

It is also contemplated that the primary supports 506 may be constructed like the shown secondary supports 516 (i.e., with high arched ribs 522 joining to the distal receptacle end 510). However, the lower ribs of the primary supports 506 such as shown in FIGS. 5A-5D may be helpful to add strength and to prevent tissue from entering the introducer tip opening 512. Alternatively, the secondary supports 516 can be structurally identical to the primary supports 506, if it is found that the added support is desirable and the restriction to flow through the introducer tip opening 512 is not unduly compromised. Other alternatives will be apparent to persons of ordinary skill in the art in view of the present disclosure.

The probe receptacle of any given embodiment may have any suitable shape to fit any desired navigation probe. The probe receptacle may be configured to fit one particular kind of probe, or it may be configured to retain a number of different navigation probes. For example, a probe receptacle as described above with reference to FIGS. 2A-5D may be configured to interchangeably receive any one of four or more different probes such illustrated in FIGS. 6A to 6D. A first probe 600 has a tip diameter D of 1.0 mm and a taper angle θ of approximately 6.0°. A second probe 602 has a tip diameter D of 0.8 mm and a taper angle θ of approximately 7.5°. A third probe 604 has a tip diameter D of 1.0 mm and a taper angle θ of approximately 18.0°. A fourth probe 606 has a tip diameter D of 1.0 mm and a 1.0 mm diameter cylindrical shaft 608 extending proximally from the tip. Each of these probes can be inserted with the probe tip seated at the distal end of the receptacle, within 1.0 mm and more preferably within 0.5 mm of the distal introducer end, to hold probe tip against lateral movement.

The receptacle may be formed such that it is not likely for the surgeon to "wedge" the probe tip in place, as this may cause difficulty with removing the probe. To this end, it is preferred for the taper angle of the receptacle's inner wall to not exactly match the taper angle of any particular probe tip in such a way to lock the two parts together. It is also preferred for the material of the receptacle to be relatively hard to prevent it from deforming to allow the probe tip to become lodged therein. Polycarbonate plastic is expected to be suitable for this purpose, but other materials may be used. Of course, a surgeon applying a very large force on the probe might lodge it in the receptacle regardless of how the receptacle is designed, so it will be understood that these preferences are predicated on normal use of the instrument and are not intended to set strict requirements for all embodiments under all circumstances.

Alternatively, the receptacle may be deliberately formed to tend to capture the probe tip in place. For example, the probe tip may include an enlarged end that snaps into a corresponding shape within the receptacle such that a force is required to remove the probe, or the receptacle may include thin deformable ribs that tend to grip the tip of the probe. This may require more care when removing the probe, but add the benefit of not requiring the surgeon to handhold the probe at all times.

The foregoing embodiments are expected to help surgeons use introducer and retractor systems with navigation systems. It is expected that surgeons will use the device by assembling the introducer with a retractor, placing the navigation probe in the introducer until the tip of the probe reaches the end of the probe receptacle, and then advancing the three parts forward into the tissue as a unit. During the process, the surgeon can remove the probe to get a better view into the introducer or to insert other instruments or devices into the introducer. If desired, a clamp or other device may be provided to hold the probe in place to free up the surgeon's hands for other tasks. Examples of clamps are disclosed in the incorporated references, but other mechanisms may be used. Other uses and methods will be apparent to those of ordinary skill in the art in view of this disclosure.

The introducer tip opening may add significant benefits to the system, such as by allowing fluids to ventilate to prevent an excessive accumulation of pressure around the introducer, allowing removal of fluids, and if the opening is large enough allowing resection or manual movement of tissue adjacent the opening. The tip opening also may allow air to vent towards the tissue as the introducer is withdrawn from the retractor after the assembly is placed at the surgery site, which can help prevent the introducer from generating suction that pulls on the tissue as the introducer is withdrawn. Other benefits will be apparent in view of the this disclosure and with further use of the system.

While it is expected that the foregoing embodiments can be used "freehand" by simply placing the probe tip 224 into the probe receptacle, in some cases a surgeon may wish to lock the probe 220 in place within the introducer 200. This may be accomplished by using a retaining mechanism, such as the exemplary probe retainer 700 shown in FIGS. 7A-8B.

The probe retainer 700 comprises a receiver 702 that is affixed to the introducer 200 by a pair of clamps 704. The receiver 702 includes a channel 706 sized to receive a probe 220. The channel 706 preferably is a closed passage having a diameter suitable to accommodate a probe 220, but it may include a longitudinal slot or have a "C" or "U" shaped profile, or the like, in other embodiments. The channel 706 has a proximal channel end 708 facing towards the surgeon, and a distal channel end 710 that extends into the introducer 200. When the probe shaft 222 is located in the channel 706, the channel 706 limits and may completely restrict movement of the probe shaft 222 in the lateral direction.

The receiver 702 may be configured to selectively lock the probe 220 in place within the channel 706. For example, the proximal channel end 708 may have a threaded outer surface 712 that is configured to engage a corresponding lock nut 714, and one or more cutout sections 716 passing through the proximal channel end 708. The threaded outer surface 712 and lock nut 714 are configured such that the lock nut 714 compresses the threaded outer surface 712 as it is tightened onto the threaded outer surface 712, such as by providing one or both with a slight taper or making the lock nut's threads slightly smaller in diameter than the threads on the outer threaded surface 712. The cutout sections 716 provide reliefs to allow the threaded surface 712 to move inwards as the lock nut 714 is tightened. Thus, as the lock nut 714 is tightened on the threaded outer surface 712, the threaded outer surface 712 moves radially inwards, and an inner surface 718 of the proximal channel end 708 clamps against and secures the probe 220 in place. The receiver 702 also may include one or more retaining lips 720 to prevent the lock nut 714 from being fully removed from the receiver 702.

Other locking mechanisms may be used in other embodiments. For example, the lock nut 714 may be replaced by a band clamp, a set screw, or other devices. Examples of alternative locks are provided in the incorporated references, and other options will be apparent to the person of ordinary skill in the art in view of this disclosure.

In the shown embodiment, the receiver 702 may include a number of slots 722 (e.g., three slots) that extend proximally from the distal channel end 710. The exemplary slots 722 extend longitudinally along the longitudinal axis 212 of the assembly, but other orientations may be used (e.g. helical). The inner surface of the channel 706 is also may be gently tapered such that the diameter of the channel 706 decreases as it approaches the distal channel end 710. The final diameter of the channel 706 at the distal channel end 710 may be slightly less than the largest diameter probe 220 expected to be used with the device, such that the probe 220 is slightly compressed by the receiver 702 at the distal channel end 710. The slots 722 allow the channel 706 to flex outwards at the distal channel end 710 to accommodate probes 220 of different sizes. This feature is expected to provide a useful slight retaining force, and may help center the probe 220 within the channel 706.

The receiver also may be configured to direct the distal probe tip 224 towards a receptacle (e.g., receptacle 230, 304, 404 or 504) as the probe 220 is installed into the introducer 200. The foregoing tapered and slotted arrangement is expected to accomplish this by orienting the channel 706 towards a corresponding receptacle at the distal introducer tip, but other embodiments may use other configurations to do the same thing. Preferably, the channel 706 extends in the longitudinal direction, so that it prevents significant angulation of the probe 220 within the channel 706 (i.e., it prevents angulation that could prevent the distal probe tip 224 from entering the receptacle). For example, the channel 706 may have an inner diameter that is no more than 110% of the largest probe diameter, and a length that is at least 300% and more preferably at least 1000% of the largest probe diameter.

Despite the foregoing, in other embodiments the channel 706 may comprise a simple ring or passage that is not tapered and does not include slots, or the taper and slots may be replaced by a flexible diaphragm or cantilevered arms that help center the probe 220 within the channel 706. Other alternatives will be apparent to persons of ordinary skill in the art in view of the present disclosure.

The clamps 704 are attached to the receiver 702, and configured to hold the receiver 702 at a fixed location relative to the introducer 200. The receiver 702 may be centered on the introducer 200, such as shown, or it may be offset from the introducer's centerline. In this embodiment, the clamps 704 are connected to the receiver 702 by clamp arms 724 that are shaped to generally match the shape of the introducer sidewall 204 at the proximal introducer end 206.

Thus, each clamp arm 724 has an opening 726 through which the surgeon can view into the introducer passage 210.

Each clamp 704 comprises a tab 728 that is shaped to receive a user's finger, and a hook 730 that is shaped to wrap around a corresponding lip 800 (FIGS. 8A-B) on the introducer. The clamp arms 724 are located between the tab 728 and the hook 730. The clamp arms 724 and hooks 730 are movable between a latched position in which the hooks 730 are relatively close to one another, and an unlatched position in which the hooks 730 are relatively far from one another. In their latched position, the hooks 730 are spaced by a first distance at which they wrap around the corresponding lips 800 to secure the probe retainer 700 to the introducer 200. The hook spacing in the latched position may be slightly greater than their natural resting position when not attached to an introducer 200. Thus, when attached to the introducer 200, the clamp arms 724 may be under a slight bending force caused by flexing the hooks 730 from their resting position to their latched position. This can help provide a stronger locking connection, and may reduce the likelihood of shifting or moving when connected.

When the surgeon pinches the tabs 728 together, the clamp arms 724 flex and provide a fulcrum about which the hooks 730 rotate until they are located at a second distance from one another. In this position, the hooks 730 release the lips 800 and the probe retainer 70 can be removed from the introducer. The clamps 704 may be reinstalled onto the introducer 200 by reversing this operation, and the hooks 730 may include ramped surfaces to allow them to be snapped onto the lips 800 simply by pressing the probe retainer 700 against the proximal introducer end 206.

In the exemplary embodiment, there are two clamp arms 724, each of which has two spaced portions that surround an opening 726 to allow visualization into the introducer 200. Each clamp arm 724 is connected to the receiver 702 at two locations on opposite sides of the receiver 702. The attachments between the receiver 702 and the clamp arms 724 may have buttresses 732 to increase the rigidity of the connection. This is expected to help the clamp arms 724 flex in a more predictable manner during the detachment and installation process.

The foregoing clamp 704 arrangement is expected to provide simple and reliable engagement to selectively connect the probe retainer 700 to the introducer 200. However, other embodiments may use different structures to hold the probe in place. For example, the flexible clamp arms 724 may be replaced by more rigid members having a mechanical pivot such as a pivot pin or the like and a return spring to bias the hooks 730 to the clamped position. As another example, each clamp arm 724 may have a single portion located on one side of the introducer 200, rather than two spaced portions, and the clamps 704 may be turned 90° relative to the shown position such that the grip the introducer 200 from the side rather than from the top. Other alternatives will be apparent to persons of ordinary skill in the art in view of the present disclosure.

FIGS. 8A and 8B show the embodiment of FIGS. 7A-B as it appears when installed on an exemplary introducer 200. The introducer 200 is shown assembled with a corresponding retractor 202. The introducer 200 preferably includes a probe tip receptacle such as those described previously herein, but it is also envisioned that the probe retainer 700 may be used with introducers that do not have a probe tip receptacle, such as those discussed with reference to FIG. 1. The assembly of the probe retainer 700 and navigation probe 220 preferably can be removed from or installed into the introducer 200 without separating the introducer 200 from the retractor 202. This provides rapid access to the introducer interior, if necessary.

It will be appreciated that the foregoing embodiments may be modified in various ways. As one example, features disclosed in one embodiment may be used with any of the other embodiments. As another example, the probe receptacles described herein can be formed integrally with the introducer by additive manufacturing or molding (the illustrated embodiments show various configurations in which conventional two-part injection molding processes may be used to make the introducer and probe receptacle as a single integrally molded part), or formed separately and attached to the introducer. As another example, the probe receptacle may have any sidewall profile shape, rather than the generally circular shapes shown in the embodiments. The probe receptacles also may have any combination of conical, cylindrical, hemispherical, or other shapes. It is also envisioned that the probe receptacle may have openings such as the flow passages of FIG. 2B and slots of the later embodiments, even when the introducer does not have an introducer tip opening, which can be beneficial to displace fluid from the receptacle to allow free entry of the probe tip. Other alternatives will be apparent to persons of ordinary skill in the art in view of the present disclosure.

The present disclosure describes a number of new, useful and nonobvious features and/or combinations of features that may be used alone or together. The embodiments described herein are all exemplary, and are not intended to limit the scope of the inventions. It will be appreciated that the inventions described herein can be modified and adapted in various and equivalent ways, and all such modifications and adaptations are intended to be included in the scope of this disclosure and the appended claims.

We claim:

1. An introducer system for use with a navigation probe having a navigation element and a navigation probe shaft having a diameter and terminating at a distal probe tip, the introducer system comprising an introducer having:

a sidewall extending along a longitudinal axis and forming an introducer passage extending from a proximal introducer end to a distal introducer end, the sidewall being larger, in a lateral direction that is orthogonal to the longitudinal axis, than the navigation probe shaft diameter;

a probe receptacle located at the distal introducer end, the probe receptacle extending along the longitudinal axis within the introducer passage from a proximal receptacle end to a distal receptacle end, the probe receptacle having an inner surface that tapers continuously from a first lateral size in the lateral direction at the proximal receptacle end to a second lateral size in the lateral direction at the distal receptacle end, the first lateral size being greater than the second lateral size;

wherein the inner surface is configured and dimensioned to receive the distal probe tip and restrict movement of the distal probe tip in the lateral direction, and the sidewall is configured and dimensioned to allow the navigation probe shaft to move in the lateral direction within the passage when the distal probe tip is positioned in the probe receptacle; and wherein the inner surface comprises a proximal portion adjacent the proximal receptacle end having a first angle relative to the longitudinal axis, and an intermediate portion located distally from the proximal portion and having a second angle relative to the longitudinal axis, the second angle being less than the first angle.

2. The introducer system of claim 1, wherein the sidewall has an elliptical profile in the lateral direction, and the probe receptacle has a circular profile in the lateral direction.

3. The introducer system of claim 1, wherein the sidewall has a sidewall profile in the lateral direction, and the probe receptacle is located at a geometric center of the sidewall profile.

4. The introducer system of claim 1, wherein the inner surface further comprises a distal portion located distally from the intermediate portion forming at least a portion of a hemispherical surface.

5. The introducer system of claim 1, wherein the probe receptacle comprises a distal receptacle opening passing through the distal receptacle end and forming a first fluid flow path between the inner surface and an exterior of the sidewall at the distal introducer end.

6. The introducer system of claim 5, further comprising an introducer tip opening forming a second fluid flow path between the introducer passage and the exterior of the sidewall at the distal introducer end.

7. The introducer system of claim 1, wherein at least a portion of the probe receptacle is spaced from the sidewall in the lateral direction by a gap.

8. The introducer system of claim 7, wherein the probe receptacle comprises at least one opening at a location between the proximal receptacle end and the distal receptacle end forming a fluid communication path between the inner surface and the gap.

9. The introducer system of claim 1, further comprising an introducer tip opening forming a fluid flow path through the sidewall at the distal introducer end.

10. The introducer system of claim 9, wherein at least a portion of the probe receptacle is spaced from the sidewall in the lateral direction by a gap.

11. The introducer system of claim 10, further comprising at least one passage through an outer wall of the probe receptacle between the proximal receptacle end and the distal receptacle end, the at least one passage forming a fluid communication path between the introducer tip opening and the gap, the fluid communication path being configured to at least partially bypass the proximal receptacle end.

12. The introducer system of claim 11, wherein the at least one passage comprises a plurality of slots extending through the outer wall of the probe receptacle, each of the plurality of slots extending along the longitudinal axis from the proximal receptacle end to a portion of the sidewall located adjacent the distal receptacle end.

13. The introducer system of claim 9, further comprising at least one passage through the inner surface to the introducer tip opening.

14. The introducer system of claim 13, wherein the at least one passage comprises one or more annular passages.

15. The introducer system of claim 9, wherein the probe receptacle overlies the introducer tip opening as viewed along the longitudinal axis and the introducer further comprises at least one fluid flow path that extends through the introducer tip opening without passing through the proximal receptacle end.

16. The introducer system of claim 15, further comprising one or more supports extending between the sidewall and the probe receptacle to suspend the probe receptacle adjacent the introducer tip opening.

17. The introducer system of claim 16, wherein the one or more supports comprises a plurality of ribs extending along the longitudinal axis.

18. The introducer system of claim 16, wherein the distal receptacle end is located within the introducer tip opening.

19. The introducer system of claim 18, wherein at least part of the one or more supports is located within the introducer tip opening.

20. The introducer system of claim 16, wherein the probe receptacle has a receptacle size in the lateral direction, and the introducer tip opening has an opening size in the lateral direction, and the receptacle size is less than the opening size.

21. The introducer system of claim 16, wherein the probe receptacle has a receptacle size in the lateral direction, and the introducer tip opening has an opening size in the lateral direction, and the opening size is less than the receptacle size.

22. The introducer system of claim 1, wherein the inner surface is configured to hold the distal probe tip adjacent the distal introducer end.

23. The introducer system of claim 22, wherein the inner surface is configured to hold the distal probe tip within 1.0 mm of the distal introducer end.

24. The introducer system of claim 1, wherein the inner surface is configured to interchangeably hold at least four different navigation probes, each navigation probe having a distal probe tip having a geometric shape that is distinct from the other navigation probes, with each of the distal probe tips located, when fully installed in the probe receptacle, within 1.0 mm of the distal introducer end.

25. The introducer system of claim 1, wherein at least a portion of the sidewall at the distal introducer end is transparent and visible from the proximal introducer end when the navigation probe is installed within the introducer.

26. The introducer system of claim 1, further comprising a probe retainer configured to selectively connect to the proximal introducer end, the probe retainer comprising a receiver configured to receive the navigation probe shaft when the probe retainer is attached to the proximal introducer end and thereby limit movement of the navigation probe shaft in the lateral direction.

27. An introducer system for use with a navigation probe having a navigation element and a navigation probe shaft having a diameter and terminating at a distal probe tip, the introducer system comprising:
an introducer having:
a sidewall extending along a longitudinal axis and forming an introducer passage extending from a proximal introducer end to a distal introducer end, the sidewall being larger, in a lateral direction that is orthogonal to the longitudinal axis, than the navigation probe shaft diameter, and
a probe receptacle located at the distal introducer end, the probe receptacle extending along the longitudinal axis within the introducer passage from a proximal receptacle end to a distal receptacle end, the probe receptacle having a conical inner surface extending from the proximal receptacle end towards the distal receptacle end, the conical inner surface tapering from a first lateral size in the lateral direction at the proximal receptacle end to a second lateral size in the lateral direction at the distal receptacle end, the first lateral size being greater than the second lateral size, and wherein the inner surface comprises a proximal portion adjacent the proximal receptacle end having a first angle relative to the longitudinal axis, and an intermediate portion located distally from the proximal portion and having a second angle relative to the longitudinal axis, the second angle being less than the first angle; and a probe retainer configured to selectively connect to the proximal introducer end, the probe retainer comprising a receiver configured to receive the navigation probe shaft and limit movement of the navigation probe shaft in the lateral direction.

28. The introducer system of claim 27, wherein the probe retainer comprises one or more clamps connected to the receiver and configured to selectively connect to the proximal introducer end.

29. The introducer system of claim 28, wherein the one or more clamps comprises two clamps, each clamp being connected to the receiver by a clamp arm having an arm opening therethrough, each arm opening being aligned with the introducer passage to provide a visual path into the introducer passage.

30. The introducer system of claim 27, wherein the receiver comprises a lock to selectively hold the navigation probe shaft.

31. An introducer system for use with a navigation probe having a navigation element and a navigation probe shaft having a diameter and terminating at a distal probe tip, the introducer system comprising an introducer having:
a sidewall extending along a longitudinal axis and forming an introducer passage extending from a proximal introducer end to a distal introducer end, the sidewall being larger, in a lateral direction that is orthogonal to the longitudinal axis, than the navigation probe shaft diameter;
a probe receptacle located at the distal introducer end, the probe receptacle extending along the longitudinal axis within the introducer passage from a proximal receptacle end to a distal receptacle end, the probe receptacle having an inner surface having a first lateral size in the lateral direction at the proximal receptacle end and a second lateral size in the lateral direction at the distal receptacle end, the first lateral size being greater than the second lateral size;
wherein the inner surface is configured and dimensioned to receive the distal probe tip and restrict movement of the distal probe tip in the lateral direction, and the sidewall is configured and dimensioned to allow the navigation probe shaft to move in the lateral direction within the passage when the distal probe tip is positioned in the probe receptacle;
wherein at least a portion of the probe receptacle is spaced from the sidewall in the lateral direction by a gap; and
wherein the probe receptacle comprises at least one opening at a location between the proximal receptacle end and the distal receptacle end forming a fluid communication path between the inner surface and the gap.

32. The introducer system of claim 31, further comprising an introducer tip opening forming a fluid flow path through the sidewall at the distal introducer end.

33. The introducer system of claim 31, wherein the at least one opening comprises a plurality of slots extending through the outer wall of the probe receptacle, each of the plurality of slots extending along the longitudinal axis from the proximal receptacle end to a portion of the sidewall located adjacent the distal receptacle end.

34. The introducer system of claim 31, further comprising a probe retainer configured to selectively connect to the proximal introducer end, the probe retainer comprising a receiver configured to receive the navigation probe shaft when the probe retainer is attached to the proximal introducer end and thereby limit movement of the navigation probe shaft in the lateral direction.

35. An introducer system for use with a navigation probe having a navigation element and a navigation probe shaft having a diameter and terminating at a distal probe tip, the introducer system comprising:
an introducer having:
a sidewall extending along a longitudinal axis and forming an introducer passage extending from a proximal introducer end to a distal introducer end, the sidewall being larger, in a lateral direction that is orthogonal to the longitudinal axis, than the navigation probe shaft diameter, and
a probe receptacle located at the distal introducer end, the probe receptacle extending along the longitudinal axis within the introducer passage from a proximal receptacle end to a distal receptacle end, the probe receptacle having an inner surface having a first lateral size in the lateral direction at the proximal receptacle end and a second lateral size in the lateral direction at the distal receptacle end, the first lateral size being greater than the second lateral size; and
a probe retainer configured to selectively connect to the proximal introducer end, the probe retainer comprising a receiver configured to receive the navigation probe shaft and limit movement of the navigation probe shaft in the lateral direction;
wherein the probe retainer comprises two clamps connected to the receiver and configured to selectively connect to the proximal introducer end, each clamp being connected to the receiver by a clamp arm having an arm opening therethrough, each arm opening being aligned with the introducer passage to provide a visual path into the introducer passage.

* * * * *